United States Patent
de Almeida et al.

(10) Patent No.: US 10,695,354 B2
(45) Date of Patent: *Jun. 30, 2020

(54) METHODS OF TREATMENT OF PARTIAL ONSET SEIZURES USING ESLICARBAZEPINE ACETATE

(71) Applicant: BIAL-PORTELA & CA S.A., S. Mameda Do Coronado (PT)

(72) Inventors: José Luís de Almeida, Arouca (PT); Patrício Manuel Vieira Araújo Soares da Silva, Oporto (PT)

(73) Assignee: Bial-Portela & CA S.A., São Mamede do Coronado (PT)

( * ) Notice: Subject to any disclaimer, the term of this patent is extended or adjusted under 35 U.S.C. 154(b) by 0 days.

This patent is subject to a terminal disclaimer.

(21) Appl. No.: 16/449,057

(22) Filed: Jun. 21, 2019

(65) Prior Publication Data

US 2019/0307765 A1    Oct. 10, 2019

Related U.S. Application Data (60) Continuation of application No. 15/422,278, filed on Feb. 1, 2017, which is a division of application No. 14/187,018, filed on Feb. 21, 2014, now abandoned, which is a continuation of application No. 13/017,732, filed on Jan. 31, 2011, now abandoned, which is a continuation of application No. 11/123,205, filed on May 6, 2005, now abandoned.

(51) Int. Cl.
*A61K 31/55* (2006.01)
*A61K 31/19* (2006.01)
*A61K 45/06* (2006.01)

(52) U.S. Cl.
CPC .............. *A61K 31/55* (2013.01); *A61K 31/19* (2013.01); *A61K 45/06* (2013.01)

(58) Field of Classification Search
CPC .................................................... A61K 31/55
See application file for complete search history.

(56) References Cited

U.S. PATENT DOCUMENTS

| | | |
|---|---|---|
| 3,489,836 A | 1/1970 | Waring |
| 3,637,661 A | 1/1972 | Schindler |
| 3,642,775 A | 2/1972 | Schindler |
| 4,076,812 A | 2/1978 | Allgeier et al. |
| 4,235,895 A | 11/1980 | Blattner et al. |
| 4,409,212 A | 10/1983 | Mondadori |
| 4,452,738 A | 6/1984 | Aufderhaar |
| 4,540,514 A | 9/1985 | Aufderhaar |
| 4,559,174 A | 12/1985 | Aufderhaar |
| 5,095,033 A | 3/1992 | Levy et al. |
| 5,368,865 A | 11/1994 | Asakura et al. |
| 5,466,683 A | 11/1995 | Sterling et al. |
| 5,472,714 A | 12/1995 | Bourquin |
| 5,496,564 A | 3/1996 | Asakura et al. |
| 5,624,945 A | 4/1997 | Bousseau et al. |
| 5,695,782 A | 12/1997 | Bourquin |
| 5,753,646 A | 5/1998 | Benés et al. |
| 5,827,819 A | 10/1998 | Yatvin et al. |
| 5,912,013 A | 6/1999 | Rudnic et al. |
| 5,980,942 A | 11/1999 | Katzhendler et al. |
| 6,296,873 B1 | 10/2001 | Katzhendler et al. |
| 6,475,510 B1 | 11/2002 | Venkatesh et al. |
| 6,534,090 B2 | 3/2003 | Puthli et al. |
| 8,288,532 B2 | 10/2012 | Learmonth et al. |
| 8,372,431 B2 | 2/2013 | Cardoso de Vasconcelos et al. |
| 9,206,135 B2 | 12/2015 | Learmonth et al. |
| 9,566,244 B2 | 2/2017 | Cardoso de Vasconcelos et al. |
| 9,643,929 B2 | 5/2017 | Learmonth et al. |
| 9,750,747 B2 | 9/2017 | Soares Da Silva |
| 9,763,954 B2 | 9/2017 | Soares Da Silva |
| 2001/0036943 A1 | 11/2001 | Coe et al. |
| 2002/0037926 A1 | 3/2002 | Lan |
| 2002/0147197 A1 | 10/2002 | Newman et al. |
| 2003/0055008 A1 | 3/2003 | Marcotte |
| 2003/0056896 A1 | 3/2003 | Jao et al. |
| 2003/0175353 A1 | 9/2003 | Dudhara et al. |
| 2003/0225002 A1 | 12/2003 | Livingstone |
| 2004/0038874 A1 | 2/2004 | Omoigui |
| 2004/0158060 A1 | 8/2004 | Learmonth |
| 2004/0162280 A1 | 8/2004 | Learmonth |
| 2004/0180816 A1 | 9/2004 | Loscher et al. |
| 2004/0185097 A1 | 9/2004 | Kannan et al. |
| 2004/0266754 A1 | 12/2004 | Learmonth |

(Continued)

FOREIGN PATENT DOCUMENTS

| | | |
|---|---|---|
| BE | 747.086 | 3/1970 |
| CA | 2 575 042 A1 | 11/1995 |

(Continued)

OTHER PUBLICATIONS

US 5,753,645 A, 05/1998, Benés et al. (withdrawn)
Almeida et al, "Pharmacokinetic Profile of BIA 2-093, a punitive new antiepileptic drug, after single and multiple administration in human healthy volunteers," Poster, Epilepsia (2002) 43(Supp 8): 146.
Ambrosio, A. et al., "Mechanisms of Action of Carbamazepine and Its Derivatives, Oxcarbazepine, BIA 2-093, and BIA 2-024*," Neurochemical Research, vol. 27, Nos. 1/2, Feb. (2002), pp. 121-130.
Berk, M. et al., "Olanzapine compared to lithium in mania: a double-blind randomized controlled trial." Int Clin Psychopharmacol, 14: 339-343 (1999).

(Continued)

*Primary Examiner* — Yong S. Chong
(74) *Attorney, Agent, or Firm* — Finnegan, Henderson, Farabow, Garret & Dunner, LLP (57) ABSTRACT

The present disclosure relates to the treatment of various diseases and conditions with eslicarbazepine acetate. The present disclosure also relates to the use of eslicarbazepine acetate in a method for reducing or decreasing epileptic seizures in a patient. The present disclosure also relates to a method for increasing the exposure to eslicarbazepine in a patient. The present disclosure also relates to a method of preparing a pharmaceutical composition comprising eslicarbazepine acetate.

27 Claims, 2 Drawing Sheets

(56) References Cited

U.S. PATENT DOCUMENTS

| | | |
|---|---|---|
| 2005/0004102 A1 | 1/2005 | Schmutz |
| 2007/0021356 A1 | 1/2007 | Cady |
| 2009/0110722 A1 | 4/2009 | Cardoso de Vasconcelos et al. |

FOREIGN PATENT DOCUMENTS

| | | |
|---|---|---|
| CA | 2 356 460 A1 | 6/2000 |
| CA | 2 370 030 A1 | 10/2000 |
| CA | 2 446 160 A1 | 12/2002 |
| CA | 2 479 672 A1 | 10/2003 |
| CA | 2 494 660 A1 | 2/2004 |
| CA | 2 497 780 A1 | 4/2004 |
| CA | 2 498 890 A1 | 4/2004 |
| CA | 2 537 088 A1 | 3/2005 |
| CA | 2 543 829 A1 | 5/2005 |
| CA | 2 553 207 A1 | 8/2005 |
| CA | 2 674 303 A1 | 7/2008 |
| DE | 2 011 045 | 10/1970 |
| EP | 0 435 826 A1 | 7/1991 |
| EP | 0 637 449 A1 | 2/1995 |
| EP | 0 646 374 A1 | 4/1995 |
| EP | 0 751 129 A1 | 1/1997 |
| EP | 1 239 832 B1 | 9/2002 |
| EP | 1 477 480 A1 | 11/2004 |
| GB | 864536 | 4/1961 |
| GB | 1 310 120 | 3/1973 |
| JP | A-2007 529564 | 10/2007 |
| RU | 2079304 | 5/1997 |
| RU | 2178298 C1 | 1/2002 |
| RU | 2236224 C2 | 9/2004 |
| WO | WO 89/05642 A1 | 6/1989 |
| WO | WO 94/13298 A1 | 6/1994 |
| WO | WO 97/02250 A1 | 1/1997 |
| WO | WO 97/38978 A1 | 10/1997 |
| WO | WO 98/17692 A1 | 4/1998 |
| WO | WO 98/35681 | 8/1998 |
| WO | WO 00/01416 A1 | 1/2000 |
| WO | WO 00/66096 A2 | 11/2000 |
| WO | WO 00/76942 A1 | 12/2000 |
| WO | WO 01/32183 A2 | 5/2001 |
| WO | WO 01/39779 A1 | 6/2001 |
| WO | WO 02/03915 A2 | 1/2002 |
| WO | WO 02/05799 A2 | 1/2002 |
| WO | WO 02/092572 A1 | 11/2002 |
| WO | WO 02/094774 A2 | 11/2002 |
| WO | WO 02/096881 A1 | 12/2002 |
| WO | WO 02/098418 A1 | 12/2002 |
| WO | WO 03/042182 A1 | 5/2003 |
| WO | WO 03/101428 A1 | 12/2003 |
| WO | WO 03/101430 A1 | 12/2003 |
| WO | WO 2004/014391 A1 | 2/2004 |
| WO | WO 2004/026314 A1 | 4/2004 |
| WO | WO 2004/031155 A1 | 4/2004 |
| WO | WO 2004/035041 A1 | 4/2004 |
| WO | WO 2004/069187 A2 | 8/2004 |
| WO | WO 2004/071152 A2 | 8/2004 |
| WO | WO 2004/071513 A1 | 8/2004 |
| WO | WO 2004/087161 A1 | 10/2004 |
| WO | WO 2004/087166 A1 | 10/2004 |
| WO | WO 2004/087168 A1 | 10/2004 |
| WO | WO 2004/099153 A1 | 11/2004 |
| WO | WO 2004/100992 A2 | 11/2004 |
| WO | WO 2004/103348 A2 | 12/2004 |
| WO | WO 2005/020968 A2 | 3/2005 |
| WO | WO 2005/092290 | 10/2005 |
| WO | WO 2005/092294 A1 | 10/2005 |
| WO | WO 2006/121363 | 11/2006 |
| WO | WO 2007/012793 | 2/2007 |
| WO | WO 2007/094694 | 8/2007 |
| WO | WO 2008/088233 | 7/2008 |
| WO | WO 2011/014084 | 2/2011 |
| WO | WO 2012/091593 | 7/2012 |

OTHER PUBLICATIONS

Bhana, N. et al. "Olanzapine: A Review of its Use in the Treatment of Bipolar I Disorder." CNS Drugs, 15: 871-904 (2001).

Bialer, M. et al., "Progress report on new antiepileptic drugs: a summary of the Seventh Eilat Conference (Eilat VII)," Epilepsy Research 61, pp. 1-48 (2004).

Bialer, "New Antiepileptic Drugs Currently in Clinical Trials: Is There a Strategy in Their Development," Therapeutic Drug Monitoring (2002) 24: 85-90.

Bonifacio, M.J. et al., "Laboratory Research: Interaction of the Novel Anticonvulsant, BIA 2-093, with Voltage-Gated Sodium Channels: Comparison with Carbamazepine," Epilepsia, 42(5):600-608, 2001.

Borges et al., "Urban Prevalence of Epilepsy: Populational Study in San Jose do Rio Preto, a medium-sized city in Brazil," Arq Neuropsiquiatr (2004) 62(2-A):199-205.

Cabrera, J. et al., "Kombinierte rezidiv-prophylaktische Behandlung der manisch-depressiven Erkrankung mit Lithium und Carbamazepin oder Oxcarbazepin," Der Nervenarzt, 58: 245-249 (1987).

Carroll, B.T. et al. "Loading Strategies in Acute Mania," CNS Spectr, 6: 919-922, 930 (2001).

Cookson, J. "Toward a Clinical Understanding of Bipolar Disorders: Classification and Presentation," Epilepsia, 46 (Suppl. 4); 3-7, 2005.

Cramer et al., "Quality of Life Improvement with conversion to lamotrigine monotherapy," Epilepsy & Behavior (2004), 5(2): 224-230.

"DSM-IV Criteria for Bipolar Disorder," Diagnostic and Statistical Manual of Mental Disorders, 4th Ed., 1994, American Psychiatric Association, pp. 350-363.

Emrich, H.M., "Studies with Oxcarbazepine (Trileptal®) in Acute Mania," Int Clin Pharmacol., 5 (Suppl 1), 83-88 (1990).

English language abstract of Cabrera, J. et al., "Kombinierte rezidiv-prophylaktische Behandlung der manisch-depressiven Erkrankung mit Lithium und Carbamazepin Oder Oxcarbazepin," Der Nervenarzt, 58:245-249 (1987).

English language abstract of Seidel, M., "Kombinierte rezidiv-prophylaktische Behandlung der manisch-depressiven Erkrangkung mit Lithium und Carbamazepin oder Oxcarbazepin," Der Nervenarzt, 59: 248-249 (1988).

English language Derwent abstract of EP 0 435 826 A1.

Gelder, M. et al., "The International Classification of Diseases (ICD)," Oxford Textbook of Psychiatry, 3rd ed., pp. 67-70 (1996).

Goodnick, P.J. et al. "Use of olanzapine in non-psychotic psychiatric disorders," Expert Opin Pharmacother, 2: 667-680 (2001).

Janowsky, D.S. "New treatments of bipolar disorder," Curr Psychiatry Rep, 1: 111-113 (1999).

Karceski et al., "The Expert Consensus Guideline Series: Treatment of Epilepsy," Epilepsy & Behavior (2001) 2: A1-A50.

Keck, P.E., Jr. et al.,"A review of randomized, controlled clinical trials in acute mania," J Affect Disord 59 (Suppl. 1): S31-S37 (2000).

Khouzam, H.R. et al, "Treatment of bipolar I disorder in an adolescent with olanzapine," J Child Adolesc Pyschopharmacol, 10:147-151 (2000).

Krämer, G. "Oxcarbazepine—Adverse Effects," Antiepileptic Drugs, 5th Ed., pp. 479-486 (2002).

Levy, R. et al. "Antiepileptic Drugs," 2002:Lippincott Williams & Wilkins, PA.

Maia, J. et al., "BIA 2-093 as add-on therapy for refractory partial epilepsy in adults," Epilepsia, vol. 45, Suppl. 3, p. 158, abstract, p. 410 (2004).

Maia et al., "Effect of Eslicarbazepine Acetate (BIA 2-093) on the Steady State Pharmacokinetics of Digoxin in Healthy Subjects," Epilepsia (2005) 46(Supp 6): 283.

Schmitz et al., "Introduction," Neurobiological Links of Epilepsy, Bipolar Disorder, and Anticonvulsants, Epilepsia, 46(Suppl. 4): 1-2 (2005).

(56) References Cited

OTHER PUBLICATIONS

Price, P.L. "Olanzapine to treat the acute mania of bipolar disorder," S D J Med, 53: 523 (2000).
Rogvi-Hansen et al, "Adverse Effects of Established and New Antiepileptic Drugs: An Attempted Comparison," Pharmac. Ther. (1995) 68(3): 425-434.
Sadock, B. et al., "Synopsis of Psychiatry—Behavioral Sciences/Clinical Psychiatry," 9th ed., p. 535.
Sander, "The Use of Antiepileptic Drugs—Principles and Practice," Epilepsia 45(Supp 6): 28-34 (2004).
Seidel, M., "Kombinierte rezidiv-prophylaktische Behandlung der manisch-depressiven Erkrangkung mit Lithium und Carbamazepin Oder Oxcarbazepin," Der Nervenarzt, 59: 248-249 (1988).
Shua-Haim, J., "Oxcarbazepine in the management of behavioral agitation in community-dwelling patients with Alzheimer's disease: An open-label study," S434, P.6.019.
Simanski, C., et al., "Akutschmerztherapie und-management in der Orthopädie," Der Orthopäde, vol. 31: 522-533 (2002).
Soares-Da-Silva et al., "Effect of Age and Gender on the Pharmacokinetics of Eslicarbazepine Acetate," Epilepsia (2005) 46(Supp 8): 216-217.
Teitelbaum, M., "Oxcarbazepine in BipolarDisorder," J Am Acad Child Adolesc Psychiatry, 40(9): 993-994 (2001).
Tohen, M. et al. "Efficacy of Olanzapine in Acute Bipolar Mania: A Double-blind, Placebo-controlled Study,"Arch Gen Psychiatry, 57: 841-849 (2000).
Tohen, M. et al. "Onset of action of antipsychotics in the treatment of mania," Bipolar Disord, 2: 261-268 (2000).
Vieta, E. et al. "Olanzapine as Long-Term Adjunctive Therapy in Treatment-Resistant Bipolar Disorder," J Clin Psychopharmacol, 21: 469-473 (2001).
Vicenzini et al., "Clinical and neuropsychological effects of Carbamazepine, Oxcarbazepine, and Levetiracetam in healthy volunteers," Boll Lega It Epil, 2002, No. 118, 173-175.
Weber, W.E.J., "Farmacotherapie van neuropathische pijn door letsel van afferente zenuwvezels," Ned Tijdschr Geneeskd 145(17): 813-817 (2001).
Wildgrube, C. "Case Studies on Prophylactic Long-term Effects of Oxcarbazepine in Recurrent Affective Disorders," Inter Clin Psychopharmacol, 5(Suppl. 1): 89-94 (1990).
Vaz-Da-Silva, M. et al., "Eslicarbazepine Acetate Pharmacokinetics after Single and Repeated Doses in Healthy Subjects," Epilepsia, 46(8): 191 (2005).
Almeida, L. et. al.; Drugs R&D, 2003, 4(5) 269-284.
Ambrosio, A.F. et. al; Neurochemical Research, Feb. 2002, 27, 1/2, 121-130.
Benes, J. et. al., J. of Medicinal Chemistry, 1999, 42 (14) 2582-2587.
Sharief, M., et. al.; Epilepsy Research; 25, (1996) 217-224.
Abraham, G. et al., "Possible Interaction of Clozapine and Lisinopril," Am. J. Psychiatry, 158:6, p. 969, Jun. 2001.
Albani, F. et al., "Oxcarbazepine—Interactions with Other Drugs," Antiepileptic Drugs, 5th ed., pp. 466-469, 2002.
Almeida, L. et al., "Once-Daily versus twice-daily therapy with the novel antiepileptic drug eslicarbazepine acetate," Department of Research and Development, BIAL (Portela & $C^a$ SA), S Mamede do Coronado, Portugal.
Almeida, L. et al., "Pharmacokinetic profile of BIA 2-093, a putative new antiepileptic drug, after single and multiple administration in human healthy volunteers," Epilepsia, vol. 43, suppl 8, P460, 2002.
Almeida, L. et al., "Safety, Tolerability and Pharmacokinetic Profile of BIA 2-093, a Novel Putative Antiepileptic Agent, during First Administration to Humans," Drugs R&D 4(5); pp. 269-284, (2003).
Almeida, L. et al., "Safety, Tolerability and Pharmacokinetic Profile of BIA 2-093, a Novel Putative Antiepileptic, in a Rising Multiple-Dose Study in Young Healthy Humans," J Clin Pharmacol 44: 906-918 (2004).

Ambrósio, A. et al., "Inhibition of glutamate release by BIA 2-093 and BIA 2-024, two novel derivatives of carbamazepine, due to blockade of sodium but not calcium channels," Biochemical Pharmacology 61:1271-1275 (2001).
Ambrósio, A. et al., "Neurotoxic/neuroprotective Profile of carbamazepine, oxcarbazepine and two new putative antiepileptic drugs, BIA 2-093 and BIA 2-024," European Journal of Pharmacology 406, pp. 191-201 (2000).
Araújo, I. et al., "Neurotoxicity Induced by Antiepileptic Drugs in Cultured Hippocampal Neurons: A Comparative Study between Carbamazepine, Oxcarbazepine, and Two New Putative Antiepileptic Drugs, BIA 2-024 and BIA 2-093," Epilepsia 45 (12); pp. 1498-1505 (2004).
Auberson, Y. et al., "N-Phosphonoalkyl-5-aminomethylquinoxaline-2,3-diones: In Vivo Active AMPA and NMDA(Glycine) Antagonists," Bioorg. Med. Chem. Lett. 9, 249-254 (1999).
Baruzzi, A. et al., "Oxcarbazepine: Pharmacokinetic Interactions and Their Clinical Relevance," Epilepsia 35 (Suppl. 3), S14-S19 (1994).
Beelen, AP et al., "Asymptomatic QTc Prolongation associated with quetiapine fumarate overdose in a patient being treated with risperidone," Human & Experimental Toxicology, No. 20, pp. 215-219 (2002).
Benes, F. et al., "GABAergic Interneurons: Implications for Understanding Schizophrenia and Bipolar Disorder," Neuropsychopharmacology,vol. 25, No. 1, pp. 1-27 (2001).
Benes, J. et al., "Anticonvulsant and Sodium Channel-Blocking Properties of Novel 10,11-Dihydro-5H-dibenz[b,f]azepine-5-carboxamide Derivatives," J. Med. Chem., 42:2582-2587 (1999).
Beydoun, A. et al., "Oxcarbazepine," Expert Opin. Pharmacother. 3(1), pp. 59-71 (2002).
Beydoun, A., "Postherpetic Neuralgia: Role of Gabapentin and Other Treatment Modalities," Epilepsia, vol. 40 (Suppl. 6), S51-S56 (1999).
Bialer, M., "Oxcarbazepine—Chemistry, Biotransformation, and Pharmacokinetics," Antiepileptic Drugs, 5th ed., 459-465, 2002.
Bonifácio, M.J. et al., "Interaction of the Novel Anticonvulsant, BIA 2-093, with Voltage-Gated Sodium Channels: Comparison with Carbamazepine," Epilespsia, 42(5):600-608 (2001).
Borowicz K. et al., "Interaction of GYKI 52466, A Selective Non-Competitive Antagonist of AMPA/Kainate Receptors, with Conventional Antiepileptic Drugs in Amygdala-kindled Seizure in Rats," Polish Journal of Pharmacology, 53: pp. 101-108 (2001).
Borowicz, K. et al., "The non-competitive AMPA/kainate receptor antagonist, GYKI 52466, potentiates the anticonvulsant activity of conventional antiepileptics," European Journal of Pharmacology 281, 319-326 (1995).
Cabrera, J.F. et al., "Long-term randomized Clinical Trial on Oxcarbazepine vs Lithium in Bipolar and Schizoaffective Disorders: Preliminary Results," Pharmacopsychiat. 19, 282-283 (1986).
Calabrese, J., "Lamotrigine and Clozapine for Bipolar Disorder," Am. J. Psychiatry, v. 157, No. 9, 1523 (2000).
Cunha, R. et al., "Effects of Carbamazepine and Novel 10,11-Dihydro-5H-Dibenz[b,f]Azepine-5-Carboxamide Derivatives on Synaptic Transmission in Rat Hippocampal Slices," Pharmacology & Toxicology, 90:208-213 (2002).
Czuczwar, S. et al., "LY 300164, a novel antagonist of AMPA/kainate receptors, potentiates the anticonvulsive activity of antiepileptic drugs," European Journal of Pharmacology, 359, 103-109 (1998).
Czuczwar, S. et al., "The New Generation of GABA Enhancers: Potential in the Treatment of Epilepsy," CNS Drugs 15(5), 339-350 (2001).
Dam, M. "Summing up of the success so far gained through choice of drugs or combination of drugs," Acta Neurologica Scandinavica, 19-22 (1984).
Dean, B. et al., "A change in the density of [$^3$H] flumazenil, but not [$^3$H]muscinmol binding, in Brodmann's Area 9 from subjects with bipolar disorder," Journal of Affective Disorders 66, 147-158 (2001).
Deckers, C. et al., "Selection of Antiepileptic Drug Polytherapy Based on Mechanisms of Action: The Evidence Reviewed," Epilepsia 41(11); 1364-1374 (2000).
Dembowski, C. et al., "Successful Antimanic Treatment and Mood Stabilization with Lamotrigine, Clozapine, and Valproate in a (56) References Cited

OTHER PUBLICATIONS

Bipolar Patient after Lithium-induced Cerebellar Deterioration," Pharmacopsychiatry, v. 36, pp. 83-86 (2003).
Dickenson, A.H. et al., "The Pharmacology of Excitatory and Inhibitory Amino Acid-Mediated Events in the Transmission and Modulation of Pain in the Spinal Cord," Gen. Pharmac. vol. 28, No. 5, pp. 633-638 (1997).
Dietrick, D.E. et al., "Oxcarbazepine in Affective and Schizoaffective Disorders," Pharmacopsychiatry, vol. 34, 242-250 (2001).
Dost, R. et al., "ELB139: a new anxiolytic compound with potent effects in rodent models for generalised and focal seizures," Abstracts from the 6th European Congress on Epileptology, Journal of the International League Against Epilepsy, Epilepsia, vol. 45, Suppl. 3, p. 116, p. 242, 2004.
Duby, J. et al., "Diabetic Neuropathy: An Intensive Review," AM J Health-Syst Pharm, vol. 61, 160-176 (2004).
Dursun, S. et al., "Clozapine Plus Lamotrigine in Treatment-Resistant Schizophrenia," Arch Gen Psychiatry, vol. 56, 950-951 (1999).
Dursun, S., "When treating patients with schizophrenia, what clinical points should be considered if lamotrigine is chosen to augment closapine?," Revue de psychiatrie & de neuroscience, v. 26, No. 2, pp. 168 (2001).
Dursun, S.M. et al., "Augmenting antipsychotic treatment with lamotrigine or topiramate in patients with treatment-resistant schizophrenia: a naturalistic case-series outcome study," Journal of Psychopharmacology 15(4), 297-301 (2001).
Eaton, M. et al., "A single intrathecal Injection of GABA permanently reverses neuropathic pain after nerve injury," Brain Research 835, 334-339 (1999).
Emrich, H.M. et al., "Action of Sodium-Valproate and of Oxcarbazepine in Patients with Affective Disorders," Anticonvulsants in Affective Disorders, 45-55 (1984).
Emrich, H.M. et al., "Current Perspectives in the Pharmacopsychiatry of Depression and Mania," Neuropharmacology, vol. 22, No. 3B, 385-388 (1983).
Emrich, H.M. et al., "The Use of Sodium Valproate, Carbamazepine and Oxcarbazepine in Patients with Affective Disorders," Journal of Affective Disorders, 8:243-250 (1985).
Emrich, H.M. et al., "Therapeutic Effects of GABA-ergic Drugs in Affective Disorders. A Preliminary Report," Pharmacology Biochemistry & Behavior, vol. 19, 369-372 (1983).
European Agency for the Evaluation of Medicinal Products, "Note for Guidance on Clinical Investigation of Medicinal Products for the Treatment and Prevention of Bipolar Disorder," CPMP/EWP/567/98 (2001).
Faigle, J. et al., "Metabolic Characteristics of Oxcarbazepine (®Trileptal) and Their Beneficial Implications for Enzyme Induction and Drug Interactions," Behavioural Neurology, vol. 3 (suppl. 1), 21-30(1990).
Farago, F. "Trigeminal Neuralgia: Its Treatment with Two New Carbamazepine Analogues," Eur. Neurol. 26, 73-83(1987).
Farooque, R., "Uncommon Side Effects Associated with Olanzapine," Pharmacopsychiatry, 36, 83-86, 2003.
Finnerup, N., "Anticonvulsants in Central Pain," Expert Opin Pharmacother 3(10): 1411-1420, (2002).
Fitzgerald, B. et al., "Elevation of Carbamazepine-10,11-Epoxide by Quetiapine," Pharmacotherapy, vol. 22, No. 11, pp. 1500-1503 (2002).
Flesch, G. et al., "Determination of the R-(–) and S-(+) enantiomers of the monohydroxylated metabolite of oxcarbazepine in human plasma by enantioselective high-performance liquid chromatography", Journal of Chromatography, 581:147-151 (1992).
Freedman, G. "Clinical management of common causes of geriatric pain," Geriatrics, 57(5): 36-41 (2002).
Garnett, W.R., "Lamotrigine—Interaction with Other Drugs," Antiepileptic Drugs, 5th ed., 380-388 (2002).
Gelenberg, A.J. et al. "Treating Bipolar Disorder: Toward the Third Millennium," Pysch. Times, Issue XVIII, Issue 4 (2001).
Gidal, B. "Topiramate—Drug Interactions," Antiepileptic Drugs, 5th ed., pp. 735-739 (2002).

Gilmer, W. "Anticonvulsants in the treatment of mood disorders: assessing current and future roles," Expert Opin. Pharmacother. 2(10):1597-1608 (2001).
Gloth, M. "Pain Management in Older Adults: Prevention and Treatment," JAGS 49:188-199 (2001).
Grant, S. et al., "Oxcarbazepine: A Review of its Pharmacology and Therapeutic Potential in Epilepsy, Trigeminal Neuralgia and Affective Disorders," Drugs 43 (6): 873-888 (1992).
Greil, W. et al., "Prophylactic Treatment of Affective Disorders With Carbamazepine and Oxcarbazepine: An Open Clinical Trial," Psychiatry, The State of the Art; vol. 3, 491-494 (1983).
Haack, K. et al., "The Catalyst Precursor, Catalyst, and Intermediate in the Ruii-Promoted Asymmetric Hydrogen Transfer between Alcohols and Ketones," Angew Chem Int Ed Eng, 36(3): 285-288 (1997).
Hagenah, U. et al., "Tuberöse Sklerose and organische bipolare Störung bei einer 15jä hrigen Jugendlichen (Tuberous sclerosis and organic bipolar disorder in a 15 year old adolescent)," Z Kinder-Jugendspychiatr, 27(4): 283-289 (1999).
Hainzl, D. et al., "Enantioselective Oxidation of 10,11-Dihydro-10-hydroxy-dibenz/b,f/azepine-5-carboxamide, An Active Metabolite of Oxcarbazepine, in the Rat," Br J Pharmacol, 127,42P.
Hainzl, D. et al., "Metabolism of two new antiepileptic drugs and their principal metabolites S(+)- and R(–)-10,11-dihydro-10-hydroxy carbamazepine," Epilepsy Research 44:197-206 (2001).
Harden, R.N., "Complex regional pain syndrome," British Journal of Anaesthesia, 87(1): 99-106 (2001).
Hirschfeld, R. et al., "A review of the evidence for carbamazepine and oxcarbazepine in the treatment of bipolar disorder," International Journal of Neuropsychopharmacology, 7: 507-522 (2004).
Homs, J. et al., "Neuromiotonia congénita. Estudio retrospectivo de cuarto casos," Neurología, 14(7): 328-337 (1999).
Hopkins, H.S. et al. "Treating Bipolar Disorder: Toward the Third Millennium," Psych. Times, vol. XVIII, Issue 2 (2001).
Hutt, A. J. et al., "Drug Chirality and its Clinical Significance," Drugs, 52 (Suppl. 5): 1-12 (1996).
Ichikawa, K. et al., "Inhibitory effect of oxcarbazepine on high-frequency firing in peripheral nerve fibers," European Journal of Pharmacology, 420: 119-122 (2001).
International Search Report and Written Opinion for International Application No. PCT/162005/002357, dated Dec. 13, 2005.
Johannessen, C., "Mechanism of action of valproate: a commentatory," Neurochemistry International, 37: 103-110 (2000).
Keck, P.E., Jr. et al., "Anticonvulsants in the Treatment of Bipolar Disorder," Journal of Neuropsychiatry, 4(4): 395-405 (1992).
Keck, P.E., Jr. et al., "Bipolar disorder," Med Clin North Am 85(3): 645-61 (2001).
Kiguchi, S. et al., "Suppressive Effects of Oxcarbazepine on Tooth Pulp-Evoked Potentials Recorded at the Trigeminal Spinal Tract Nucleus in Cats," Clinical and Experimental Pharmacology and Physiology, 28:169-175 (2002).
Learmonth, D. et al. "Synthesis, anticonvulsant properties and pharmacokinetic profile of novel 10,11-dihydro-10-oxo-5H-dibenz/b,f/azepine-5-carboxamide derivatives," Eur J Med Chem 36: 227-236 (2001).
Lemke, M. "Effect of Carbamazepine on Agitation in Alzheimer's Inpatients Refractory to Neuropleptics," J Clin Psychiatry 56(8): 354-357 (1995).
Leppik, I.E., "Antiepileptic Drugs in Development: Prospects for the Near Future," Epilepsia, 35 (Suppl. 4): S29-S40 (1994).
Lessig, M. et al., "Topirimate for Reversing Atypical Antipsychotic Weight Gain," J Am Acad Child Adolesc Psychiatry, 40(12): 1364 (2001).
Levy, E. et al., "Topiramate Produced Weight Loss Following Olanzapine-Induced Weight Gain in Schizophrenia," J Clin Psychiatry, 63(11): 1045 (2002).
Lisgarten, J. et al., "The Structure of 10, 11-Dihydro-10hydroxy-5H-dibenz[b,f]nazepine-5-carboxamide, an Anticonvulsant Drug Molecule," Acta Cryst, C45: 656-658 (1989).
Lloyd, P. et al., "Clinical Pharmacology and Pharmacokinetics of Oxcarbazepine," Epilepsia, 35 (Suppl. 3): S10-S13 (1994).

(56) References Cited

OTHER PUBLICATIONS

Löscher, W. "Valproate: A Reappraisal of its Pharmacodynamic Properties and Mechanisms of Action," Progress in Neurobiology vol. 58, pp. 31-59 (1999).

Maia, J. et al., "Effect of eslicarbazepine acetate (BIA 2-093) on the steady-state pharmacokinetics of digoxin in healthy subjects," poster at 26th International Epilepsy congress, (2005).

Maia, J. et al., "Effect of Food on the Pharmacokinetic Profile of Eslicarbazepine Acetate (BIA 2-093)," Drugs in R&D, 6(4): 201-206 (2005).

Margineanu, D.G. et al., "UCB 34714, a new pyrrolidone anticonvulsant, had no effect on voltage-gated potassium currents in cultured mouse hippocampal neurons," Abstracts from the 6th European Congress on Epileptology, Journal of the International League Against Epilepsy, Epilepsia, vol. 45, Suppl. 3, p. 116 (2004).

May, T.W. et al., "Fluctuations of 10-hydroxy-carbazepine during the day in epileptic patients," Acta Neurol Scand 93: 393-397 (1996).

McElroy, S. et al., "Pharmacologic Agents for the Treatment of Acute Bipolar Mania," Biol Psychiatry, 48: 539-557 (2000).

McLean, M., "Oxcarbazepine—Mechanisms of Action," Antiepileptic Drugs, 5th Ed., pp. 451-458 (2002).

Meldrum, B. "Pharmacology of GABA," Clinical Neuropharmacology vol. 5, No. 3, pp. 293-316 (1982).

"The Merck Manual," 1406-1408, (1999).

Meyerson, B. et al., "Modulation of Spinal Pain Mechanisms by Spinal Cord Stimulation and the Potential Role of Adjuvant Pharmacotherapy," Stereotact Funct Neurosurg, 68:129-140 (1997).

Mohar, B. et al., "Highly enantioselective synthesis via dynamic kinetic resolution under transfer hydrogenation using Ru($\eta^6$-arene)-N-perfluorosulfonyl-1,2-diamine catalysts: a first insight into the relationship of the ligand's $pK_a$ and the catalyst activity" Chem Commun, pp. 2572-2573 (2001).

Müller, A. et al., "Carbamazepine and Oxacarbazepine in the Treatment of Manic Syndromes—Studies in Germany," Anticonvulsants in Affective Disorders, pp. 139-147 (1984).

Müller, A. et al., "Oxcarbazepine in Acute Mania," Psychiatry, The State of the Art, vol. 3, pp. 495-500 (1985).

Navarro, V. et al., "Topiramate for Clozapine-Induced Seizures," Am J Psychiatry, 158(6): 968-969, 2001.

Nunes, T. et al., "Eslicarbazepine acetate (BIA 2-093): Relative bioavailability and bioequivalence of 50 mg/mL oral suspension and 200 mg and 800 mg tablet formulations," poster at 26th Internat' Drugs R & D, 6, 4, 253-260 (2005).

"Oxcarbazepine," The Lancet, 196-198 (1989).

"Panel Discussion," Epilepsia, 40 (Suppl. 6): S73-S74, 1999.

Parada, A. et al., "The novel anticonvulsant BIA 2-093 inhibits transmitter release during opening of voltage-gated sodium channels: a comparison with carbamazepine and oxcarbazepine," Neurochemistry International, 40: 435-440 (2002).

Pavuluri, M. et al., "Topiramate Plus Risperidone for Controlling Weight Gain and Symptoms in Preschool Mania," Journal of Child and Adolescent Psychopharmacology, vol. 12, No. 3, 271-273 (2002).

Petty, F. "GABA and mood disorders: a brief review and hypothesis," J Affective Disorders 34: 275-281 (1995).

Petty, F. et al., "Low Plasma GABA Is a Trait-Like Marker for Bipolar Illness,"Neurophyschopharmacology, vol. 9, No. 2, pp. 125-132 (1993).

Pisani, F. et al., "Lamotrigine—Adverse Effects," Antiepileptic Drugs, 5th ed., pp. 408-416 (2002).

Post, R.M. et al., "The place of anticonvulsant therapy in bipolar illness," Psychopharmacology 128: 115-129 (1996).

Rosenberg, J. et al., "The Effect of Gabapentin on Neurophathic Pain," The Clinical Journal of Pain, 13: 251-255 (1997).

Rosner, H. et al., "Gabapentin Adjunctive Therapy in Neuropathic Pain States," The Clinical Journal of Pain, 12: 56-58(1996).

Rowbotham, M.et al., "Gabapentin for the Treatment of Postherpectic Neuralgia," JAMA, vol. 280, No. 21, pp. 1837-1842 (1994).

Saba, G. et al., "Lamotrigine—Clozapine Combination in Refractory Schizophrenia: Three Cases," J. Neuropsychiatry Clin Neurosc 14(1): 86 (2002).

Scheyer, R.D., "Valproic Acid—Drug Interactions," Antiepileptic Drugs, 5th ed., pp. 801-807 (2002).

Schmidtz, B. et al, "Introduction," Epilepsia, vol. 46 (Suppl. 4): 1-2 (2005).

Schmutz, M. et al., "Oxcarbazepine: Preclinical Anticonvulsant Profile and Putative Mechanisms of Action," Epilepsia, vol. 35 (Suppl. 5): S47-S50 (1994).

Schütz, H. et al., "The metabolism of $^{14}$C-oxcarbazepine in man," Xenobiotica, vol. 16(8): 769-778 (1986).

Sierra-Paredes, G. et al., "Effect of novel anticonvulsant BIA 2-093 on seizures induced by picrotoxin microperfusion in the rat hippocampus," Abstracts from the 6th European Congress on Epileptology, Journal of the International League Against Epilepsy, Epilepsia, vol. 45, Suppl. 3, p. 116, p. 243, 2004.

Silveira, P. et al. "BIA 2-093 pharmacokinetics in healthy elderly subjects," Epilesspsia, 45 (Supple. 3), 157 (2004).

Stiller, C. et al., "Release of γ-Aminobutyric Acid in the Dorsal Horn and Suppression of Tactile Allodynia by Spinal Cord Stimulation in Mononeuropathic Rats," Neurosurgery, vol. 39(2): 367-375 (1996).

"Strategies to Control Pain in Older Persons: Highlights of Recent Guidelines," Consultant, vol. 42(11): 1373-1376 (2002).

Stubley, L. et al, "Only Early Intervention with Gama-Aminobutyric Acid Cell Therapy Is Able to Reverse Neuropathic Pain After Partial Nerve Injury," J. Neurotrauma, vol. 18(4): 471-477 (2001).

Świąlder, M. et al., "Influence of LV 300164, An AMPA/Kainate Receptor Antagonist Upon the Anticonvulsant Action of Antiepileptic Drugs Against Aminophylline-Induced Seizures in Mice," Pol J Pharmacol, 55: 103-107 (2003).

Taran, F. et al. "High-Throughput Screening of Enantioselective Catalysts by Immunoassay," Angew. Chem. Int. Ed., 41(1): 124-127 (2002).

Tartara, A. et al., "The pharmacokinetics of oxcarbazepine and its active metabolite 10-hydroxy-carbazepine in healthy subjects and in epileptic patients treated with phenobarbitone or valproic acid," Br J Clin Pharmac, 36: 366-368 (1993).

Trimble, M., "Oxcarbazepine—Clinical Efficacy and Use in Psychiatric Disorders," Antiepileptic Drugs, 5th Ed., pp. 476-478 (2002).

Vartiainen, H. et al., "Carbamazepine and Oxcarbazepine in the Treatment of Aggression," Psychopharmacology, vol. 114(3): B13, abstract 44 (1994).

Vaz-da-Silva, M. et a., "Influence of food on the pharmacokinetics of the antiepileptic agent BIA 2-093," Abstracts from the 6th European Congress on Epileptology, Journal of the International League Against Epilepsy, Epilepsia, vol. 45, Suppl. 3, p. 157, p. 408, 2004.

Velikonja, M. et al, "Effect of Oxcarbazepone (CG 47.680) on Affective and Schizoaffective Symptoms—A Preliminary Report," Anticonvulsants in Affective Disorders, pp. 208-210 (1984).

Volosov, A. et al., "Comparative Stereoselective Pharmacokinetic Analysis of 10-Hydroxycarbazepine After Oral Administration of its Individual Enantiomers and the Racemic Mixture to Dogs," Epilepsia, Vo. 41(9): 1107-1111 (2000).

Volosov, A. et al., "Enantioselective pharmacokinetics of 10-hydroxycarbazepine after oral administration of oxcarbazepine to healthy Chinese subjects," vol. 66(6): 547-553 (1999).

Volosov, A. et al., "Stereoselective Pharmacokinetic Analysis of the Antiepileptic 10-Hydroxycarbazepine in Dogs," Therapeutic Drug Monitoring, 21: 219-223 (1999).

Von Unruh, G.E. et al., "Gas Chromatographic Assay for Oxcarbazepine and its Main Metabolites in Plasma," Journal of Chromatography Biomedical Applications, vol. 345(1): 67-76 (1985).

Walden, J. et al., "Bedeutung alter and neuer Antiepileptika in der Behandlung psychischer Erkrankungen (Significance of Old and New Antiepileptic Drugs in the Treatment of Psychiatric Diseases)," Fortschr Neurol Psychiat, 63: 320-335 (1995).

Wang, P. W. et al., "Gabapentin augmentation therapy in bipolar depression," Bipolar Disorders, 4: 296-301 (2002).

(56) References Cited

OTHER PUBLICATIONS

Zakrzewska, J.M. et al. "Oxcarbazepine: a new drug in the management of intractable trigeminal neuralgia," Journal of Neurology, Neurosurgery, and Psychiatry, 52: 472-476 (1989).
Zarnowski, T. et al., "NBQX—A Selective AMPA Antagonist Enhances Antiepileptic Properties of Common Anticonvulsant Drugs Against Maximal Electroshock in Mice," Polish J Pharmacology & Pharmacy, vol. 44: 258-259 (1992).
Almeida, L. et al., "A Double-Blind, Add-On, Placebo-Controlled Exploratory Trial of Eslicarbazepine Acetate in Patients with Partial-Onset Seizures," Epilepsia, AES Proceedings, 2005, Abstract 2.229, pp. 167-168.
Almeida, L. et al., "Single-Dose and Steady-State Pharmacokinetics of Eslicarbazepine Acetate (BIA 2-093) in Healthy Elderly and Young Subjects," Journal of Clinical Pharmacology, 2005, 45: 1062-1066.
Augusteijn, R. et al., "Oxcarbazepine (Trileptal, OXC)—Dose-Concentration Relationship in Patients with Epilepsy," Acta. Neurolo. Scan., Proceedings of the Northern European Epilepsy Symposium, 37:82(S133), G10, 1990.
Bialer, M., "Pharmacokinetic Evaluation of Sustained Release Formulations of Antiepileptic Drugs," Clinical Pharmacokinet. 22(1): 11-21, 1992.
Bill, P.A. et al., "A Double-Blind Controlled Clinical Trial of Oxcarbazepine Versus Phenytoin in Adults with Previously Untreated Epilepsy," Epilepsy Research, 27, pp. 195-204, (1997).
Christe, W. et al., "A Double-Blind Controlled Clinical Trial: Oxcarbazepine Versus Sodium Valproate in Adults with Newly Diagnosed Epilepsy," Epilepsy Research, 26, pp. 451-460, (1997).
Collins, R.J. et al., "Extended Release Formulations of Anticonvulsant Medications," CNS Drugs 2000, Sep. 14(3): pp. 203-212.
Dam, M. et al., "A Double-Blind Study Comparing Oxcarbazepine and Carbamazepine in Patients with Newly Diagnosed, Previously Untreated Epilepsy," Epilepsy Res., 3(1989), p. 70-76.
Ficker, D.M., et al., "Improved Tolerability and Efficacy in Epilepsy Patients with Extended-Release Carbamazepine," Neurology 65: p. 593-595, Aug. (2 of 2) 2005.
Friis, M.L. et al., "Therapeutic Experiences with 947 Epileptic Out-Patients in Oxcarbazepine Treatment," ACTA Neurologica Scandinavica, 1993, 87(3): pp. 224-227.
Levy, G., "A Pharmacokinetic Perspective on Medicament Non-Compliance," Clinical Pharmacology & Therapeutics, vol. 54, No. 3, pp. 242-244, Sep. 1993.
Marmarou, A. et al., "Zonisamide: Physician and Patient Experiences," Epilepsy Research, 64 (2005), pp. 63-69.
"Oxcarbazepine for Epilepsy—A Useful New Choice?", Drug & Therapeutics Bulletin, vol. 40, No. 6, pp. 46-48, Jun. 2002.
"Oxcarbazepine," New Medicines on the Market, UK Medicines Information, Monograph No. 4/00/15, pp. 1-5, Aug. 2000.
Pellock, J.M. et al., "Extended-Release Formulations: Simplifying Strategies in the Management of Antiepileptic Drug Therapy," Epilepsy & Behavior, 5 (2004), pp. 301-307.
Reinikainen, K.J. et al., "Comparison of Oxcarbazepine and Carbamazepine: A Double-Blind Study," Epilepsy Res., 1 (1987), pp. 284-289.
Schachter, S.C. et al., "Oxcarbazepine, Double-Blind, Randomized, Placebo-Controled, Monotherapy Trial for Partial Seizures," Neurology, 52: pp. 732-737, Mar. (1 of 2) 1999.
Stefan, H. et al., "Clinical Monitoring During Carbamazepine Slow-Release, Once-Daily Monotherapy," Epilepsia, vol. 29, No. 5, pp. 571-577, 1988.
Urquhart, J., "Ascertaining How Much Compliance is Enough with Outpatient Antibiotic Regimens," Postgrad Med. J. (1992) 68 (Suppl. 3), pp. S49-S59.
Van Parys, J.A.P. et al., "Survey of 260 Epileptic Patients Treated with Oxcarbazepine (Trileptal®) on a Named-Patient Basis," Epilepsy Research 19 (1994) pp. 79-85.
French, J.A. "Refractory Epilepsy: One Size Does Not Fit All," Epilepsy Currents, 2006, 6(6): 177-180.

Potschka, H. et al., "Inhibition of multidrug transporters by verapamil or probenecid does not alter blood-brain barrier penetration of levetiracetam in rats", Epilepsy Research 58, 85-91, (2004).
Potschka , H. et al., "In Vivo Evidence for P-Glycoprotein-Mediated Transport of Phenytoin at the Blood-Brain Barrier of Rats", Epilepsia, 42, 1231-1240, 2004.
Sharief, M., "Double-blind, placebo-controlled study of topiramate in with refractory partial epilepsy", Epilepsy Research 25 (1996) 217-224.
Simanski, C. et al., "Acute Pain Therapy and Management in Orthopedics," Der Orthopäde, vol. 31: 522-533 (2002).
Weber, W.E.J., "Pharmacotherapy of neuropathic pain cuased by damage to afferent nerve fibres", Ned Tijdschr Geneeskd 2001, Apr. 28, 2001, 145 (17), 1-5. (English translation).
Cramer JA, Glassman M, Rienzi V. The relationship between poor medication compliance and seizures. Epilepsy Behav. Aug. 2002; 3(4):338-342.
French JA, Baroldi P, Brittain ST, Johnson JK; Prosper Investigators Study Group. Efficacy and safety of extended-release oxcarbazepine (OxtellarXR™) as adjunctive therapy in patients with refractory partial-onset seizures: a randomized controlled trial. Acta Neurol Scand. Mar. 2014;129(3):143-53.
Steinhoff BJ. Oxcarbazepine extended-release formulation in epilepsy. Expert Rev Clin Pharmacal. Mar. 2009;2(2):155-62.
Theis, J.G.W. et al, "Lack of Pharmacokinetic Interaction between Oxcarbazepine and Lamotrigine," Neuropsychopharmacology (2005), vol. 30, pp. 2269-2274.
Medical Consultation & New Remedies, 1982, vol. 18, No. 2, pp. 245-250 (with partial translation).
English-language translation of Medical Consultation & New Remedies, 1982, vol. 18, No. 2, pp. 245-250.
English-language translation of Russian Application No. RU 2178298 C1, dated Jan. 20, 2002 (6 pages).
English-language translation of Russian Application No. RU 2236224 C2, dated Sep. 20, 2004 (3 pages).
Almeida, L. et al. "Effect of gender on the eslicarbazepine acetate pharmacokinetics in health subjects," J. Clin Pharmacology, poster at 26th International Epilepsy Congress (2005).
Almeida. Luis, et al., "Eslicarbazepine Acetate (BIA 2-093)," Neurotherapeutics: The Journal of the American Society for Experimental NeuroTherapeutics, Jan. 2007, vol. 4, No. 1, pp. 88-96, The American Society for Experimental NeuroTherapeutics, Inc.
Ambrosio, A. et al., "Mechanisms of Action of Carbamazepine and Its Derivatives, Oxcarbazepine, BIA 2-093, a vd BIA 2-024*," Neurochemical Research, vol. 27, Nos. 1/2, Feb. (2002), pp. 121-130.
Ben-Menachem, E., et al., "Eslicarbazepine Acetate as Adjunctive Therapy in Adult Patients with Partial Epilepsy", Epilepsy Research, 2010, pp. 1-8, Elsevier B.V.
French, JA et al. "Efficacy and safety of an extended-release oxcarbazepine (Oxtellar XR™) as adjunctive therapy in patients with refractory partial-onset seizures: a randomized controlled trial," Acta Neurol Scand 2014, 129:143-153.
Ghose, K. et al., "Once daily dosage versus divided daily doses of carbamazepine therapy in epileptic patients: a pilot study," Pharmatherapeutica, 1981, 3(1): 71-78 (abstract only).
Ghose, K. et al., "Effect of Dosage Frequency of Carbamazepine on Drug Serum Levels in Epileptic Patients," Eur J Clin Pharmacol, 1983, 24: 375-381.
McKee, PJW. et al., "Double dummy comparison between once and twice daily dosing with modified-release carbazepine in epileptic patients," Br J Clin Pharmac, 1993, 36: 257-261.
Shorvon, Simon, "Oxcarbazepine: a review," Seizure, 2000, vol. 9, pp. 75-79, BEA Trading Ltd.
Świąder, M. et al., "Influence of LY 300164, An AMPA/Kainate Receptor Antagonist Upon the Anticonvulsant Action of Antiepileptic Drugs Against Aminophylline-Induced Seizures in Mice," Pol J Pharmacol, 55: 103-107 (2003).
Weisler, RH et al., "Efficacy and Safety of Once-versus Twice-Daily Carbazepine Extended-Release Capsules for the Treatment of Manic Symptoms in Patients with Bipolar I Disorder," Psychiatry (Edgmont), 2008, 5(3): 35-48.

(56) References Cited

OTHER PUBLICATIONS

Berkow, R., Medical Manual—Diagnostics and Therapy, Medicine Handbook, M., Mir, 1997, vol. 1, p. 982.
Berkow, R., Medical Manual—Diagnostics and Therapy, Medicine Handbook, M., Mir, 1997, vol. 1, p. 982 (English-language translation).
Berkow, R., Medical Manual—Diagnostics and Therapy, Medicine Handbook, M., Mir, 1997, vol. 1, Chap. 121, pp. 979-980 (3 pages).
Berkow, R., Medical manual—Diagnostics and Therapy, Medicine Handbook, M., Mir, 1997, vol. 1, Chap. 121, pp. 979-980 (English-language translation) (4 pages).
"Diagnosis and Management of Epilepsy in Adults," Apr. 2003, 54 pages, Scottish Intercollegiate Guidelines Network.
Abbott, N. Joan, et al., "Drug resistance in epilepsy: the role of the blood-brain barrier," Mechanisms of Drug Resistance in Epilepsy: Lessons From Oncology, 2002, pp. 38-53, Novartis Foundation.
Aronica, E., et al., "Expression and cellular distribution of multidrug transporter proteins in two major causes of medically intractable epilepsy: focal cortical dysplasia and glioneuronal tumors," Neuroscience, 2003, vol. 118, pp. 417-429, Elsevier Science Ltd.
Aronica, Eleonora, et al., "Expression and cellular distribution of multidrug resistance-related proteins in the hippocampus of patients with mesial temporal lobe epilepsy," Epilepsia, 2004, vol. 45, No. 5, pp. 441-451, International League Against Epilepsy.
Bazil, Carl W., "Epilepsy and sleep disturbance," Epilepsy and Behavior, 2003, vol. 4, pp. S39-S45, Elsevier, Inc.
Betts, Tim, et al., "Clinical experience of marketed Levetiracetam in an epilepsy clinic—a one year follow up study," Seizure, 2003, vol. 12, pp. 136-140, BEA Trading Ltd.
Clinkers, Ralph, et al., "Quantitative in vivo microdialysis study on the influence of multidrug transporters on the blood-brain barrier passage of oxcarbazepine: concomitant use of hippocampal monoamines as pharmacodynamic markers for the anticonvulsant activity," The Journal of Pharmacology and Experimental Therapeutics, 2005, vol. 314, No. 2, p. 725-731, The American Society for Pharmacology and Experimental Therapeutics, XP008091105.
Dombrowski, Stephen M., et al., "Overexpression of multiple drug resistance genes in endothelial cells from patients with refractory epilepsy," Epilepsia, 2001, vol. 42, No. 12, pp. 1501-1506, International League Against Epilepsy.
Feldmann, K. F., et al., "Pharmacokinetics and metabolism of GP 47 680, a compound related to carbamazepine, in animals and man," Advances in Epileptology, 1978, pp. 290-294, Swets & Zeitlinger B.V.
Feldmann, K. F., et al., "Pharmacokinetics and metabolism of GP 47 779, the main human metabolite of oxcarbazepine (GP 47 680) in animals and healthy volunteers," Advances in Epileptology, The XIIth Epilepsy International Symposium, 1981, pp. 89-96, Raven Press Books Ltd.
Fontes-Ribeiro, C., et al., "Eslicarbazepine acetate (BIA 2-093): Relative bioavailability and bioequivalence of 50 mg/mL oral suspension and 200 mg and 800 mg tablet formulations," Drugs R & D, 6 (5) 253-260 (2005).
French, J.A., et al., "Efficacy and tolerability of the new antiepileptic drugs II: Treatment of refractory epilepsy", Neurology, 2004, pp. 1261-1273, vol. 62, AAN Enterprises, Inc.
Gerk, Philip M., et al., "Regulation of expression of the multidrug resistance-associated protein 2 (MRP2) and its role in drug disposition," The Journal of Pharmacology and Experimental Therapeutics, 2002, vol. 302, No. 2, pp. 407-415, The American Society for Pharmacology and Experimental Therapeutics.
Kondratieva, T.C. et al., "Drug Formulation Technology," Technology of Dosage Forms, 1991, vol. 1, p. 97.
English-language translation of Kondratieva, T.C. et al., "Drug Formulation Technology," Technology of Dosage Forms, 1991, vol. 1, p. 97.
Kortekaas, Rudie, et al., "Blood-brain barrier dysfunction in parkinsonian midbrain in vivo," Annals of Neurology, Feb. 2005, vol. 57, No. 2, pp. 176-179, American Neurological Association.

Kwan, Patrick, et al., "Early identification of refractory epilepsy," The New England Journal of Medicine, Feb. 3, 2000, vol. 342, No. 5, pp. 314-319, Massachusetts Medical Society.
Kwan, Patrick, et al., "Potential role of drug transporters in the pathogenesis of medically intractable epilepsy," Epilepsia, 2005, vol. 46, No. 2, pp. 224-235, International League Against Epilepsy.
Loscher, Wolfgang, et al., "Drug resistance in brain diseases and the role of drug efflux transporters," Nature Reviews Neuroscience, Aug. 2005, vol. 6, pp. 591-602, Nature Publishing Group.
Loscher, Wolfgang, et al., "New horizons in the development of antiepileptic drugs: the search for new targets," Epilepsy Research, 2004, vol. 60, pp. 77-159, Elsevier.
Loscher, Wolfgang, et al., "Role of drug efflux transporters in the brain for drug disposition and treatment of brain diseases," Progress in Neurobiology, 2005, vol. 76, pp. 22-76, Elsevier Ltd.
Marchi, Nicola, et al., "A pilot study on brain-to-plasma partition of 10, 11-dyhydro-10-hydroxy-5H-dibenzo(b,f) azepine-5-carboxamide and MDR1 brain expression in epilepsy patients not responding to oxcarbazepine," Epilepsia, 2005, Voi 46, No. 10, pp. 1613-1620, International League Against Epilepsy, XP008091107.
Marchi, Nicola, et al., "Significance of MDR1 and multiple drug resistance in refractory human epileptic brain," BMC Medicine, 2004, vol. 2, No. 37, 10 pages, BioMed Central.
May, Theodor W., et al., "Clinical pharmacokinetics of oxcarbazepine," Clinical Pharmacokinetics, 2003, vol. 42, No. 12, pp. 1023-1042, Adis Data Information B.V.
Mohanraj, Rajiv, et al., "Pharmacological outcomes in newly diagnosed epilepsy," Epilepsy and Behavior, 2005, vol. 6, pp. 382-387, Elsevier Inc.
Oxford Dictionary of Biochemistry and Molecular Biology, 1997, Oxford University Press, p. 288.
Patsalos, Philip N., et al., "Clinically important drug interactions in epilepsy: general features and interactions between antiepileptic drugs," Neurology, Jun. 2003, pp. 347-356, vol. 2, The Lancet.
Potschka, Heidrun, et al., "Multidrug resistance protein MRP2 contributes to blood-brain barrier function and restricts antiepileptic drug activity," The Journal of Pharmacology and Experimental Therapeutics, 2003, vol. 306, No. 1, pp. 124-131, The American Society for Pharmacology and Experimental Therapeutics.
Potschka, Heidrun, et al., "P-glycoprotein and multidrug resistance-associated protein are involved in the regulation of extracellular levels of the major antiepileptic drug carbamazepine in the brain," Neuropharmacology and Neurotoxicology, Nov. 16, 2001, vol. 12, No. 16, pp. 3557-3560, NeuroReport.
Potschka, Heidrun, et al., "P-glycoprotein-mediated efflux of phenobarbital, lamotrigine, and felbamate at the blood-brain barrier: evidence from microdialysis experiments in rats," Neuroscience Letters, 2002, vol. 327, pp. 173-176, Elsevier Science Ireland Ltd.
Racine, Ronald, et al., "Modification of seizure activity by electrical stimulation: III. mechanisms," Electroencephalography and Clinical Neurophysiology, 1972, vol. 32, pp. 295-299, Elsevier Publishing Company.
Rizzi, Massimo, et al., "Limbic seizures induce p-glycoprotein in rodent brain: functional implications for pharmacoresistance," The Journal of Neuroscience, Jul. 15, 2002, vol. 22, No. 14, pp. 5833-5839.
Rowland and Tozer, Clinical Pharmacokinetics, Concepts and Applications, 1995, Lippincott Williams and Wilkins, 3d. Ed., pp. 89-90.
Scheffer, George L., et al., "Drug resistance molecules: lessons from oncology," Novartis Foundation Symposium 243, 2002, pp. 19-37, Wiley, Chichester.
Schinkel, Alfred H., et al., "Mammalian drug efflux transporters of the ATP binding cassette (ABC) family: an overview," Advanced Drug Delivery Reviews, 2003, vol. 55, pp. 3-29, Elsevier Science B.V.
Schinkel, Alfred H., et al., "P-glycoprotein in the blood-brain barrier of mice influences the brain penetration and pharmacological activity of many drugs," Journal of Clinical Investigation, Jun. 1996, vol. 97, No. 11, pp. 2517-2524, The American Society for Clinical Investigation, Inc.
Schmidt, D., et al., "Recommendations on the clinical use of oxcarbazepine in the treatment of epilepsy: a consensus view," Acta Neurologica Scandinavica, 2001, vol. 104, pp. 167-170, Munksgaard.

(56) References Cited

OTHER PUBLICATIONS

Schmidt, Dieter, et al., "Drug resistance in epilepsy: putative neurobiologic and clinical mechanisms," Epilepsia, 2005, vol. 46, No. 6, pp. 858-877, International League Against Epilepsy.
Shneker, Bassel F., et al., "Epilepsy," Jul. 2003, pp. 426-478, vol. 49, Mosby, Inc.
Sills, Graeme J., et al., "P-glycoprotein-mediated efflux of antiepileptic drugs: preliminary studies in mdrla knockout mice," Epilepsy and Behavior, 2002, vol. 3, pp. 427-432, Academic Press.
Sisodiya, S. M., et al., "Drug resistance in epilepsy: expression of drug resistance proteins in common causes of refractory epilepsy," Brain, 2002, vol. 125, pp. 22-31, Oxford University Press.
Sisodiya, Sanjay M., "Mechanisms of antiepileptic drug resistance," Current Opinion in Neurology, 2003, vol. 16, pp. 197-201, Lippincott Williams & Wilkins.
Soares-Da-Silva, P., "BIA 2-093," Epilepsy Research, 2004, vol. 61, pp. 4-6.
Sperling, Michael R., "The consequences of uncontrolled epilepsy," CNS Spectrums, Feb. 2004, vol. 9, No. 2, pp. 98-109.
Summers, Monica A., et al., "Use of verapamil as a potential p-glycoprotein inhibitor in a patient with refractory epilepsy," The Annals of Pharmacotherapy, Oct. 2004, vol. 38, pp. 1631-1634.
The Handbook of Clinical Trials and Other Research, 2002, Radcliffe Medical Press Ltd., pp. 247-251.
Tishler, David M., "MDR1 gene expression in brain of patients with medically intractable epilepsy," Epilepsia, 1995, vol. 36, No. 1, pp. 1-6, International League Against Epilepsy.
Van Vliet, Erwin, et al., "Selective and persistent upregulation of mdrlb mRNA and p-glycoprotein in the parahippocampal cortex of chronic epileptic rats," Epilepsy Research, 2004, vol. 60, pp. 203-213, Elsevier B.V.
Volk, H. A., et al., "Increased expression of the multidrug transporter p-glycoprotein in limbic brain regions after amygdala-kindled seizures in rats," Epilepsy Research, 2004, vol. 58, pp. 67-79, Elsevier B.V.
Volk, H. A., et al., "Neuronal expression of the drug efflux transporter p-glycoprotein in the rat hippocampus after limbic seizures," Neuroscience, 2004, vol. 123, pp. 751-759, Elsevier Ltd.
Wheeler-Aceto, Helen, et al., "Standardization of the rat paw formalin test for the evaluation of analgesics," Psychopharmacology, 1991, vol. 104, pp. 35-44, Springer-Verlag.
Eiger et al., "Eslicarbazepine acetate: a double-blind, add-on, placebo-controlled exploratory trial in adult patients with partial-onset seizures," *Epilepsia*, 48(3):497-504 (2007).
Nunes et al., "Steady-state plasma and cerebrospinal fluid pharmacokinetics and tolerability of eslicarbazepine acetate and oxcarbazepine in healthy volunteers," *Epilepsia*, 54(1):108-116 (2013).
Prescribing Information for Tegretol® and Tegretol®-XR, T2000-04, © Novartis.
Prescribing Information for Trileptal®, T2005, © Novartis.
Eiger et al., "Pharmacokinetics and tolerability of eslicarbazepine acetate and oxcarbazepine at steady state in healthy volunteers," Epilepsia, 2013, 54(8):1453-1461.
Ben-Menachem, "Eslicarbazepine acetate: a well-kept secret"? Epilepsy Curr., 2010, 10(1):7-8.
Prescribing Information for Aptiom®, 2013, 25 pages.
Prescribing Information for Topamax®, 2005, 49 pages.
Prescribing Information for Neurontin®, 2005, 29 pages.
Prescribing Information for Keppra®, 2005, 30 pages.
Zhang et al., "In vitro transport profile of carbamazepine, oxcarbazepine, eslicarbazepine acetate, and their active metabolites by human P-glycoprotein," Epilepsia, 2011, 52(10):1894-1904.
Fortuna et al., "Evaluation of the permeability and P-glycoprotein efflux of carbamazepine and several derivatives across mouse small intestine by the Ussing chamber technique," Epilepsia, 2012, 53(3):529-538.
Intravooth et al., "Antiepileptic drugs-induced hyponatremia: review and analysis of 560 hospitalized patients," Epilepsy Research, manuscript accepted on Mar. 28, 2018, 18 pages.

Almeida et al., Pharmacokinetics, efficacy, and tolerability of eslicarbazepine acetate in children and adolescents with epilepsy, J. Clin. Pharmacol., 2008, 48(8):966-977.
Ariens, Stereochemistry: a source of problems in medicinal chemistry, Med Res Rev, 1986, 6(4):451-466.
Ariens, Racemic therapeutics—Problems all along the line. In: Chirality in Drug Design and Synthesis, Academic Press Ltd., London, 1990, 29-43.
Balant et al., Prodrugs for the improvement of drug absorption via different routes of administration, Eur J Drug Metab Pharmacokinet, 1990, 15(2):143-153.
Bubert et al., Synthesis of water-soluble aminosulfonamide ligands and their application in enantioselective transfer hydrogenation, Tetrahedron Letters, 2001, 42:4037-4039.
Buhler, Polyvinylpyrrolidone excipients for pharmaceuticals, 2005, 125 pages.
Bundgaard, Design of bioreversible drug derivatives and the utility of the double prodrug concept, in Bioreversible Carriers in Drug Design: Theory and Application, ISBN 0080346812, Pergamon Press, 1987, 13-94.
Cayen, Racemic mixtures and single stereoisomers: industrial concerns and issues in drug development, Chirality, 1991, 3:94-98.
Dam, Potential antiepileptic drugs: oxcarbazepine, in Antiepileptic Drugs, Third Edition, Ed. R. Levy et al., New York: Raven Press, Ltd., 1989, pp. 913-924.
De Camp, The FDA perspective on the development of stereoisomers, Chirality, 1989, 1(1):2-6.
Degen, The influence of food on the disposition of the antiepileptic oxcarbazepine and its major metabolites in healthy volunteers, Biopharm Drug Dispos, 1994, 15(6):519-526.
Cho, An efficient method for removal of ruthenium byproducts from olefin metathesis reactions, Organic Letters, 2003, 5(4):531-533.
Elger, Efficacy and safety of eslicarbazepine acetate as adjunctive treatment in adults with refractory partial-onset seizures: A randomized, double-blind, placebo-controlled, parallel-group phase III study, Epilepsia, 2009, 50(3):454-463.
Eugene et al., $GABA_A$ receptor γ-2 subunit mutations linked to epileptic syndromes differentially affect phasic and tonic inhibition, The Journal of Neuroscience, 2007, 27(51):14108-14116.
French et al., Historical control monotherapy design in the treatment of epilepsy, Epilepsia, 2010, 51(10), 1936-1943.
Gelisse et al., Worsening of seizures by oxcarbazepine in juvenile idiopathic generalized epilepsies, Epilepsia, 2004, 45(10):1282-1286.
Gil-Nagel et al., Efficacy and safety of 800 and 1200 mg eslicarbazepine acetate as adjunctive treatment in adults with refractory partial-onset seizures, Acta Neural Scand, 2009, 120:281-287.
Halasz et al., Long-term efficacy and safety of eslicarbazepine acetate: results of a 1-year open-label extension study in partial-onset seizures in adult with epilepsy, Epilepsia, 2010, 51(10):1963-1969.
Excerpt from Hancock et al., The relative densities of pharmaceutical powders, blends, dry granulations, and immediate-release tablets, Pharm. Technol., 2003, 9 pages.
Higuchi, Prodrug and drug delivery—An overview, in Bioreoersible Carriers in Drug Design Theory and Application, ISBN: 0080346812, Pergamon Press, 1987, 1-12.
Jensen et al., Oxcarbazepine, Epilepsy Res Suppl, 1991, 3:135-140.
Khattab et al., Effect of mode of incorporation of disintegrants on the characteristics of fluid-bed wet-granulated tablets, J. Pharm. Pharmacol., 1993, 45:687-691.
Koch et al., Oxcarbazepine versus carbamazepine monotherapy for partial onset seizures, Cochrane Database Syst Rev, 2009, vol. 4:CD006453.
Liu et al., The mechanism of carbamazepine aggravation of absence seizures, J. Pharmacal. & Exper. Therapeutics, 2006, 319(2):790-798.
Macdonald et al., Sites of drug metabolism, prodrugs and bioactivation, Comprehensive Medicinal Chemistry, the Rational Design, Mechanistic Study & Therapeutic Application of Chemical Compounds, ISBN: 00803 70616 (vol. 5), Pergamon Press, 1990, 111-141.

(56) References Cited

OTHER PUBLICATIONS

Menge et al., Determination of oxcarbazepine in human plasma by high-performance liquid chromatography, J Chromatogr, 1983, 275(1):189-194.

Milovan et al., Effect of eslicarbazepine acetate and oxcarbazepine on cognition and psychomotor function in healthy volunteers, Epil. & Behav., 2010, 18:366-373.

Morozowich et al., Application of physical organic principles to prodrug design, Design of biopharmaceutical properties through prodrugs and analogs, ISBN: 0917330161, Washington, DC, American Pharmaceutical Association, 1977, 344-391.

Muller et al., Oxcarbazepine versus phenytoin monotherapy for epilepsy, Cochrane Database Syst Rev., 2006, 2:CD003615, 27 pages.

Mullin, Crystallization, 2001 (4th ed.), Chapter 7, pp. 289-314.

Otsuka et al., Effect of polymorphic forms of bulk powders on pharmaceutical properties of carbamazepine granules, Chem. Pharm. Bull., 1999, 47(6):852-856.

Pegot et al., First application of chiral ionic liquids in asymmetric Baylis-Hillman reaction, Tetrahedron Letters, 2004, 45(34):6425-6428.

Perucca, The clinical pharmacology of the new antiepileptic drugs, Pharmacol Res, 1993, 28(2):89-106.

Pond et al., First-pass elimination. Basic concepts and clinical consequences, Clin Pharmacokinet, 1984, 9(1):1-25.

Rauchenzauner et al., Update on treatment of partial onset epilepsy: Role of eslicarbazepine, Neuropsychiatr Dis Treat, 2010, 6:723-730.

Rauws et al., Current regulatory (draft) guidance on chiral medicinal products: Canada, EEC, Japan, United States, Chirality, 1994, 6(2):72-75.

Remington: The Science and Practice of Pharmacy, 2000 (20th ed.), cover, copyright page, and p. 552-587.

Rogawski et al., The neurobiology of antiepileptic drugs, Nat Rev Neurosci, 2004, 5(7):553-564.

Sachdeo et al., Improved quality of life in patients with partial seizures after conversion to oxcarbazepine monotherapy, Epilepsy Behav, 2006, 9(3):457-463.

Schmidt et al., Oxcarbazepine for treatment of partial epilepsy: a review and recommendations for clinical use, Epilepsy. Behav., 2000, 1(6):396-405.

Schmidt et al., Recommendations on the clinical use of oxcarbazepine in the treatment of epilepsy: a consensus view, Acta Neurol Scand, 2001, 104(3):167-170.

Schwabe, Oxcarbazepine: clinical development program, Epilepsia, 1994, 35(5):S51-S53.

Shorvon, The Treatment of Epilepsy, 3rd edition, Eds. Perucca & Engel, 2009, Chapter 38, pp. 485-498.

Sierra-Paredes et al., Effect of esicarbazepine acetate (BIA 2-093) on Latrunculin A-induced seizures and extracellular amino acid concentrations in the rat hippocampus, Epil. Res., 2007, 77:36-43.

Sinkula et al., Rationale for design of biologically reversible drug derivatives: prodrugs, J Pharm Sci, 1975, 64(2):181-210.

Sperling et al., Eslicarbazepine acetate as adjunctive therapy in patients with uncontrolled partial-onset seizures: Results of a phase III, double-blind, randomized, placebo-controlled trial, Epilepsia, 2015, 56(2):244-253.

Sperling et al., Efficacy and safety of conversion to monotherapy with eslicarbazepine acetate in adults with uncontrolled partial-onset seizures: A randomized historical-control phase III study based in North America, Epilepsia, 2015, 56(4):546-555.

Stella et al., Prodrugs. Do they have advantages in clinical practice? Drugs, 1985, 29(5):455-473.

Tan et al., Reduced cortical inhibition in a mouse model of familial childhood absence epilepsy, Proc Natl Acad Sci USA, 2007, 104:17536-17541.

Theisohn et al., Disposition of the antiepileptic oxcarbazepine and its metabolites in healthy volunteers, Eur J Clin Pharmacol, 1982, 22(6):545-551.

Wad, Simultaneous determination of eleven antiepileptic compounds in serum by high-performance liquid chromatography, J Chromatogr, 1984, 305(1):127-133.

Williams, Clinical significance of esterases in man, Clin Pharmacokinet, 1985, 10(5):392-403.

Wu et al., Insight into and practical application of pH-controlled asymmetric transfer hydrogenation of aromatic ketones in water, Angew. Chem. Int. Ed., 2005, 44:3407-3411.

Zheng et al., Oxcarbazepine, not its active metabolite, potentiates $GABA_A$ activation and aggravates absence seizures, Epilepsia, 2009, 50(1):83-87.

Aerosil 200 Product Information, 2 pages.

CHMP Assessment Report for Zebinx, dated Feb. 19, 2009, 80 pages.

The European Agency for the Evaluation of Medicinal Products, Committee for Proprietary Medicinal Products (CPMP), Note for Guidance on Specification Limits for Residues of Metal Catalysts ("EMEA Guidance"), dated Feb. 21, 2008, 34 pages.

U.S. Department of Health and Human Services, Food and Drug Administration, Center for Drug Evaluation and Research, Guideline for Submitting Supporting Documentation in Drug Applications for the Manufacture of Drug Substances ("FDA Guideline"), dated Feb. 1987, 21 pages.

U.S. Department of Health and Human Services, Food and Drug Administration, Center for Drug Evaluation and Research, Guidance for Industry: Q3A Impurities in New Drug Substances ("FDA Guidance Q3A"), 2008, 17 pages.

CAS Registry No. 236295-14-5, dated Sep. 1, 1999, 3 pages.

CAS Registry No. 298-46-4, dated Nov. 16, 1984, 7 pages.

"Guideline on strategies to identify and mitigate risks for first-in-human and early clinical trials with investigational medicinal products," European Medical Agency, 2007, 12 pages.

Bialer et al., "Pharmacokinetics and Drug Interactions of Eslicarbazepine Acetate," Epilepsia, 1-12, 2012, doi: 10.1111/j.1528-1167.2012.03519.x.

Galiana et al., "Eslicarbazepine Acetate: A New Improvement on a Classic Drug Family for the Treatment of Partial-Onset Seizures," Drugs R D., 17:329-339, 2017.

METHODS OF TREATMENT OF PARTIAL ONSET SEIZURES USING ESLICARBAZEPINE ACETATE

CROSS-REFERENCE TO RELATED APPLICATIONS

This application is a continuation of U.S. patent application Ser. No. 15/422,278, filed Feb. 1, 2017, which is a division of U.S. patent application Ser. No. 14/187,018, filed Feb. 21, 2014, which is a continuation of U.S. patent application Ser. No. 13/017,732, filed Jan. 31, 2011, which is a continuation of U.S. patent application Ser. No. 11/123,205, filed May 6, 2005, all of which are incorporated herein by reference.

BACKGROUND

The present disclosure relates to a pharmaceutical composition and a treatment method using eslicarbazepine acetate.

Epilepsy, pain conditions such as trigeminal neuralgia, and affective brain disorders such as bipolar disorder are commonly treated with carbamazepine. Treatment with carbamazepine, however, can lead to serious side effects due to the production of toxic metabolites. Oxcarbazepine was developed to reduce the severity of those side effects, but oxcarbazepine has a greatly reduced potency. See, e.g., Almeida, L. & Soares-da-Silva, P., "Safety, Tolerability, and Pharmacokinetic Profile of BIA 2-093, a Novel Putative Antiepileptic, in a Rising Multiple-Dose Study in Young Healthy Humans," *J. Clin. Pharmacol.*, 44, 906-918 (2004) (herein referred to as "Almeida I").

Thus, there is a need for a pharmaceutical composition and method for treating various conditions or diseases such as, for example, epilepsy, trigeminal neuralgia, and affective brain disorders, that has a high potency and a low occurrence of side effects.

SUMMARY

Eslicarbazepine acetate, (S)-(−)-10-acetoxy-10,11-dihydro-5H-dibenz/b,f/azepine-5-carboxamide ("BIA 2-093"), is a new drug currently being developed which is useful for the treatment of various conditions, such as, for example, epilepsy and affective brain disorders, as well as pain conditions and nervous function alterations in degenerative and post-ischemic diseases. Although chemically related to carbamazepine and oxcarbazepine, eslicarbazepine acetate is believed to avoid the production of certain toxic metabolites (such as, for example, epoxides) and to avoid the unnecessary production of enantiomers or diastereoisomers of metabolites and conjugates, without losing pharmacological activity. See Benes et al., "Anticonvulsant and Sodium Channel-Blocking Properties of Novel 10,11-Dihydro-5H-dibenz[b,f]azepine-5-carboxamide Derivatives," *J. Med. Chem.*, 42, 2582-2587 (1999).

Like carbamazepine and oxcarbazepine, eslicarbazepine acetate is believed to be a voltage-gated sodium channel (VGSC) blocker that competitively interacts with site 2 of the inactivated state of the sodium channel. The affinity for this state of the channel is similar to that of carbamazepine, while the affinity for the resting state of the channel is about 3-fold lower than that of carbamazepine. This profile may suggest an enhanced inhibitory selectivity of eslicarbazepine acetate for rapidly firing neurons over those displaying normal activity. See Bonifacio et al., "Interaction of the Novel Anticonvulsant, BIA 2-093, with Voltage-Gated Sodium Channels: Comparison with Carbamazepine," *Epilepsia*, 42, 600-608 (2001).

Evaluation of the metabolic profile of eslicarbazepine acetate, following chiral analysis, in liver microsomes from rats, dogs, monkeys and humans was found to give the S(+) enantiomer of licarbazepine, (S)-(+)-10,11-dihydro-10-hydroxy-5H dibenz/b,f/azepine-5-carboxamide (also known as "eslicarbazepine"), and not the R(−) form of licarbazepine, (R)-(−)-10,11-dihydro-10-hydroxy-5H dibenz/b,f/azepine-5-carboxamide (also known as "R-licarbazepine").

Studies in humans have shown that, after oral administration, eslicarbazepine acetate appears to be rapidly and extensively metabolized to the active metabolite eslicarbazepine and, in a minor extent, to R-licarbazepine. See Silveira et al., "BIA 2-093 Pharmacokinetics in Healthy Elderly Subjects," *Epilepsia*, 45 (suppl. 3), 157 (2004). For example, the plasma concentrations of the parent drug (eslicarbazepine acetate) have been systematically found below the limit of quantification (LOQ) of the assay (10 ng/mL). See Almeida I; Almeida, L. & Soares-da-Silva, P., "Safety, Tolerability and Pharmacokinetic Profile of BIA 2-093, a Novel Putative Antiepileptic Agent, during First Administration to Humans," *Drugs R&D*, 4, 269-284 (2003) (herein referred to as "Almeida II"). When a non-chiral method is used, the assay does not distinguish between eslicarbazepine and the R-enantiomer, and the mixture was reported as "BIA 2-005" or "racemic licarbazepine."

The inventors performed entry-into-man studies in healthy subjects, the results of which they described in the Almeida I and Almeida II articles, both of which are hereby incorporated by reference. In these studies, the healthy subjects received a single oral dose of eslicarbazepine acetate wherein the dose ranged from 20 mg to 1200 mg (see Almeida II), and multiple daily-doses of eslicarbazepine acetate ranging from 200 mg twice-daily to 1200 mg once-daily (see Almeida I). Further studies (not yet published) by the inventors have investigated higher doses of eslicarbazepine acetate, including, for example, doses ranging up to 2400 mg once-daily. The studies showed that BIA 2-005 maximum observed plasma concentration ($C_{max}$) was attained at about 1 hour to about 4 hours post-dose ($t_{max}$), the extent of systemic exposure to BIA 2-005 was approximately dose-proportional, and steady-state of BIA 2-005 plasma concentrations was attained at about 4 to 5 days. The mean renal clearance of BIA 2-005 from plasma was about 20-30 mL/min, and the total amount of BIA 2-005 recovered in the urine was approximately 20% and 40% within 12 hours and 24 hours post-dose, respectively.

The studies also showed that the apparent terminal half-life of BIA 2-005 ranged from about 8 hours to about 17 hours. See, e.g., Almeida II.

U.S. Pat. No. 6,296,873 discloses a sustained release delivery system for carbamazepine, which has a half-life ranging from 25 hours to 85 hours. To avoid adverse effects, U.S. Pat. No. 6,296,873 teaches that the carbamazepine should be administered in tablet form up to two or more times daily to slowly release the compound to maintain concentration levels between 4-12 µg/m L. Such a delivery system requires a form that is capable of delivering the compound over an extended period of time, such as a tablet form.

In one aspect of the present disclosure, the inventors have unexpectedly discovered an enhanced efficacy of eslicarbazepine acetate in the treatment of various conditions, such as, for example, the treatment of epilepsy, using once-daily administration compared to twice-daily administration. This discovery is particularly surprising because the apparent half-life of eslicarbazepine acetate ($t_{1/2}$=about 8 hours to about 17 hours) is significantly shorter than the half-life of carbamazepine ($t_{1/2}$=25 hours to 85 hours), a compound typically administered 3-4 times daily.

In another aspect of the present disclosure, the inventors have also unexpectedly discovered an enhanced exposure to eslicarbazepine after once-daily administration of eslicarbazepine acetate versus the twice-daily regimen in humans. Once-daily administration of eslicarbazepine acetate surprisingly provides an increase of exposure to eslicarbazepine than the same drug dosage divided into twice-daily doses.

DETAILED DESCRIPTION

The foregoing and following aspects and embodiments, including the studies discussed herein, are described and illustrated in a manner intending to be exemplary only, and should not be construed as limiting in scope.

One aspect of the present disclosure relates to a method for treating at least one disease or condition in a patient in need thereof by administering a pharmaceutical composition comprising eslicarbazepine acetate in a pharmacologically effective amount.

In one exemplary embodiment of the present disclosure, the pharmaceutical composition comprising eslicarbazepine acetate is administered in a once-daily dosing regimen.

In another exemplary embodiment of the present disclosure, the pharmaceutical composition is administered in a dosage intended to maximize the total exposure to eslicarbazepine, as measured by the rate of exposure and extent of exposure ($C_{max}$ and $AUC_{0-\tau}$).

In an exemplary embodiment of the present disclosure, the at least one disease or condition treated may be chosen from, for example, epilepsy, central and peripheric nervous system disorders, affective disorders, schizoaffective disorders, bipolar disorders, attention disorders, anxiety disorders, neuropathic pain and neurophratic pain-related disorders, sensorimotor disorders, vestibular disorders, and nervous function alterations in degenerative and post-ischemic diseases.

Examples of affective disorders include depression, premenstrual dysphoric disorder, post-partum depression, post-menopausal depression, anorexia nervosa, bulimia nervosa, and neurodegeneration-related depressive symptoms.

The methods disclosed in the present disclosure may be used to treat schizoaffective disorders such as, for example, schizodepressive syndromes, schizophrenia, extreme psychotic states, schizomanic syndromes, dysphoric and aggressive behavior, episodic dyscontrol or intermittent explosive disorder, and borderline personality disorder.

Bipolar disorders that may be treated according to the methods of the present disclosure include, for example, bipolar disorder and unstable bipolar disorder with rapid fluctuations (rapid cyclers), manic-depressive disorders, acute mania, mood episodes, and manic and hypomanic episodes Examples of attention disorders include attention deficit hyperactivity disorders and other attention disorders, such as, for example, autism.

Anxiety disorders may include conditions such as, for example, social anxiety disorders, post traumatic stress disorder, panic, obsessive-compulsive disorder, alcoholism, drug withdrawal syndromes, and cravings.

The neuropathic pain and neurophratic pain-related disorders that may be treated according to the methods of the present disclosure include, by way of example, neuropathic pain and associated hyperalgesia, including trigeminal, herpetic, post-herpetic and tabetic neuralgia, diabetic neuropathic pain, migraines, tension-type headaches, causalgia, and deafferentation syndromes such as, for example, brachial plexus avulsion.

Examples of sensorimotor disorders include Restless legs syndrome, spasticity, hemifacial spasm, nocturnal paroxysmal dystonia, brain ischemia associated motor and sensitive deficits, Parkinson's disease and parkinsonian disorders, antipsychotic-induced motor deficits, tardive dyskinesia, episodic nocturnal wandering, and myotonia.

Exemplary vestibular disorders include Tinnitus or other inner ear/cochlear excitability related diseases, such as, for example, neuronal loss, hearing loss, sudden deafness, vertigo, and Meniere's disease.

In other exemplary embodiments, the at least one disease or condition may be chosen from epilepsy, bipolar disorder, and trigeminal neuralgia. In yet another embodiment, the disease may be refractory partial epilepsy.

One skilled in the art will understand that these conditions are exemplary only, and will understand from the disclosure what other diseases and conditions would be considered to be within the scope of the present disclosure.

Another aspect of the present disclosure relates to a pharmaceutical composition comprising eslicarbazepine acetate and at least one pharmaceutical excipient, at least one auxiliary substance, at least one carrier material, or combinations thereof.

A further aspect of the present disclosure relates to a method of preparing a pharmaceutical composition comprising combining eslicarbazepine acetate with at least one excipient, at least one auxiliary substance, at least one carrier material, or combinations thereof. Suitable excipients, carrier materials, and other auxiliary substances which would be useful in the present invention are known to those skilled in the art, and would be readily determined. Methods for preparing pharmaceutical compositions are also known to those skilled in the art.

In one exemplary embodiment of the present disclosure, the pharmaceutical composition may be in tablet form and may comprise at least one excipient, auxiliary substance, and/or carrier material. The at least one excipient, auxiliary substance, and/or carrier material may be chosen from, for example, povidone, croscarmellose sodium, magnesium stearate, saccharin sodium, dibasic calcium phosphate dihydrate, sodium lauryl sulphate, flavorings, and combinations thereof. Exemplary tablets may be formed using granulation liquids, such as, for example, purified water and ethanol.

In another exemplary embodiment of the present disclosure, the pharmaceutical composition may be in oral suspension form and may comprise at least one excipient, auxiliary substance, and/or carrier material. The at least one excipient, auxiliary substance, and/or carrier material may be chosen from, for example, xantham gum, macrogol stearate (such as, for example, Myrj 59 P, produced by UNIQEMA), methylparaben, propylparaben, saccharin sodium, sorbitol, buffers, flavorings, and combinations thereof.

Another aspect of the present disclosure relates to a method for reducing or decreasing the number, duration, or frequency of epileptic seizures in a patient by administering to the patient a dose of a pharmaceutical composition comprising eslicarbazepine acetate in a pharmacologically effective amount. In one exemplary embodiment of the present disclosure, the method for reducing epileptic seizures in patients comprises administering a once-daily dose of the pharmaceutical composition comprising a pharmacologically effective amount of eslicarbazepine acetate.

The present disclosure also relates to a method for increasing the exposure to eslicarbazepine in a patient by administering to the patient a pharmaceutical composition comprising eslicarbazepine acetate in an amount effective to increase the plasma concentration of eslicarbazepine over the dosage interval. In one exemplary embodiment, the exposure to eslicarbazepine may be increased by delivering the pharmaceutical composition in a manner that minimizes the number of daily doses. In a further exemplary embodiment of the present disclosure, the method for increasing the exposure to eslicarbazepine in the patient comprises administering to a patient a once-daily dose of a pharmaceutical composition comprising an amount of eslicarbazepine acetate effective to increase the plasma concentration of eslicarbazepine over the dosage interval.

In a further exemplary embodiment of the present disclosure, the active ingredient of the pharmaceutical composition may consist essentially of eslicarbazepine acetate.

In a further aspect of the present disclosure, eslicarbazepine acetate may be administered to a patient in an amount resulting in a maximum plasma concentration ($C_{max}$) of eslicarbzepine greater than about 7,400 ng/mL. In other exemplary embodiments, eslicarbazepine acetate may be administered to a patient in an amount resulting in a $C_{max}$ of eslicarbazepine greater than about 12,000 ng/mL or greater than about 16,100 ng/mL. In further exemplary embodiments, eslicarbazepine acetate may be administered to a patient in an amount resulting in an area under the concentration curve (which corresponds to the extent of systemic exposure) over the dosing interval ($AUC_{0-\tau}$) of eslicarbazepine greater than about 22,700 ng/mL, such as greater than about 36,500 ng/ml, greater than about 45,200 ng/mL, or more.

In a further exemplary embodiment, eslicarbazepine acetate may be administered to a patient in an amount resulting in a maximum plasma concentration ($C_{max}$) of eslicarbzepine up to about 58,800 ng/mL or up to about 67,800 ng/mL. In a further exemplary embodiment, eslicarbazepine acetate may be administered to a patient in an amount resulting in a maximum plasma concentration ($C_{max}$) of eslicarbzepine up to about 885,000 ng/mL or up to about 1,000,000 ng/mL.

For example, a once-daily dose of about 400 mg may be administered to a patient resulting in a maximum plasma concentration ($C_{max}$) of eslicarbazepine greater than about 7,400 ng/mL. As a further example, a once-daily dose of about 800 mg or about 1200 mg may be administered to a patient resulting in a $C_{max}$ of eslicarbazepine greater than about 16,100 ng/mL or greater than about 22,700 ng/mL, respectively. In other examples, eslicarbazepine acetate may be administered in a once-daily dose greater than about 1200 mg, such as about 1800 mg or about 2400 mg, to result in a $C_{max}$ of eslicarbazepine greater than about 36,500 ng/mL, about 45,200 ng/mL, respectively.

In a further aspect of the present disclosure, eslicarbazepine acetate may be administered to a patient in an amount resulting in an area under the concentration curve (which corresponds to the extent of systemic exposure) over the dosing interval ($AUC_{0-\tau}$) of eslicarbazepine greater than about 110,000 ng·h/mL. In other exemplary embodiments, eslicarbazepine acetate may be administered to a patient in an amount resulting in an $AUC_{0-\tau}$ of eslicarbazepine greater than about 240,000 ng·h/mL or greater than about 375,000 ng·h/mL, respectively. In other examples, eslicarbazepine acetate may be administered to a patient in an amount resulting in an $AUC_{0-\tau}$ of eslicarbazepine greater than about 595,000 ng·h/mL, greater than about 790,000 ng·h/mL, or more.

For example, a once-daily dose of about 400 mg may be administered resulting in an area under the concentration curve (which corresponds to the extent of systemic exposure) over the dosing interval ($AUC_{0-\tau}$) of eslicarbazepine greater than about 110,000 ng·h/mL. In other exemplary embodiments, a once-daily dose of about 800 mg or about 1200 mg may be administered resulting in an $AUC_{0-\tau}$ of eslicarbazepine greater than about 240,000 ng·h/mL or greater than about 375,000 ng·h/mL, respectively. In other examples, eslicarbazepine acetate may be administered in a once-daily dose greater than about 1200 mg, such as about 1800 mg, about 2400 mg, or more, to result in a respective $AUC_{0-\tau}$ of eslicarbazepine greater than about 595,000 ng·h/mL, greater than about 790,000 ng·h/mL, or more.

In one exemplary embodiment of the present disclosure, a once-daily dose may be administered in a dosage comprising at least about 400 mg of eslicarbazepine acetate. In another exemplary embodiment, a once-daily dose may be administered in a dosage comprising an amount of eslicarbazepine acetate ranging from about 800 mg to about 1200 mg. In further exemplary embodiments, a once-daily dose may be administered in a dosage comprising an amount of eslicarbazepine greater than about 1200 mg, such as about 1800 mg, about 2400 mg, or more.

The pharmaceutical composition comprising eslicarbazepine acetate may optionally be administered by any route known to those skilled in the art, and may be in a form chosen from, for example, tablets or oral suspensions, or other forms.

The term "about" as used herein is meant to signify that the number modified by the term may be considered an approximation that may vary depending upon the desired properties or effect sought by the particular application, and thus should be considered to encompass the range that one of skill in the art would understand to achieve the desired or recited properties or effect.

A "method of treating" as described herein refers to administering to a patient the compound described in any amount effective to reduce the effects of, counteract, or eliminate the disease or condition being treated, or the symptoms thereof.

A "method for increasing the exposure to eslicarbazepine in a patient" as described herein refers to administering to a patient the compound described in any amount effective to increase the plasma concentration of eslicarbazepine in the patient over the dosage interval. This may, for example, be an increase due to once-daily dosing relative to twice-daily dosing.

"Reducing epileptic seizures in a patient" as described herein refers to any decrease in the number, duration, or frequency of epileptic seizures in a patient relative to the number, duration, or frequency of epileptic seizures experienced by the patient without treatment.

A "pharmacologically effective amount" of eslicarbazepine acetate in a pharmaceutical composition as described herein refers to any amount sufficient to have the desired pharmacological activity.

All effective amounts as described herein will vary according to various well-known and understood factors, such as, for example, the condition being treated and the physiological characteristics of the patient being treated. Accordingly, the effective amount will be well within the ability of one skilled in the art to determine.

Study Materials and Methods

The following demonstrates, as one example of the present disclosure, the determination and administration of an effective amount of a pharmaceutical composition comprising eslicarbazepine acetate to treat epilepsy in patients in need thereof. The effective amount of a pharmaceutical composition to treat other diseases and/or conditions would be determinable by one skilled in the art based on the techniques and concepts disclosed herein and known in the art.

The effects of eslicarbazepine acetate in humans was studied in at least the following clinical studies. In the first study, a placebo-controlled therapeutic exploratory study, once-daily and twice-daily dosing was compared in epileptic patients refractory to standard anti-epileptic drug therapy. In the second study, healthy subjects received either a once-daily (o.d.) oral dose of 900 mg of eslicarbazepine acetate or a twice-daily (b.i.d.) dose of 450 mg of eslicarbazepine acetate. In the third study, healthy subjects received single oral doses of eslicarbazepine acetate ranging from 20 mg to 2400 mg, and repeated once-daily (o.d.) oral doses ranging from 400 mg to 2400 mg of eslicarbazepine acetate.

The bioequivalence of tablets and oral suspensions was proven in a relative bioavailability study.

Study in Epileptic Patients

This clinical trial was a double-blind, randomized, placebo-controlled study performed by 20 centers in Croatia, Czech Republic, Germany, Lithuania and Poland. The stated objectives of the study were to assess the efficacy and safety of BIA 2-093 as adjunctive therapy in patients with refractory partial epilepsy. In total, 143 patients aged 18-65 years with at least 4 partial-onset seizures per month in spite of treatment with 1 or 2 antiepileptic drugs (AEDs) (e.g., phenytoin, valproate, primidone, phenobarbital, lamotrigine, gabapentin, topiramate or clonazepam) were randomly assigned to one of three groups: treatment with placebo (n=47), BIA 2-093 once-daily (n=50), or BIA 2-093 twice-daily (n=46), during 12 weeks (plus 1 week of tapering off). For the first 4 weeks, daily dose was 400 mg. Then, daily doses were increased to 800 mg (weeks 5-8), and finally to 1200 mg (weeks 9-12). Tablets with strengths of 200 mg, 400 mg, and 600 mg eslicarbazepine acetate and placebo tablets were manufactured by BIAL (S. Mamede do Coronado, Portugal) in accordance with Good Manufacturing Practice. The assay plasma to determine the concentration of BIA 2-005 was performed with a non-chiral method using isocratic liquid chromatography (LC) with single quadrupole mass spectrometric detection (MS), as described herein. See, e.g., Almeida I and Almeida II.

Study in Healthy Human Volunteers

Trial A

This human pharmacology trial was a study to investigate the steady-state pharmacokinetics of once-daily and twice-daily regimens of eslicarbazepine acetate in healthy subjects. The study was a single center, open-label, randomized, two-way crossover study in 12 healthy volunteers (6 males and 6 females) that consisted of two 8-day treatment periods separated by a washout period of 10-15 days. On each of the treatment periods the volunteers received either a daily oral dose of eslicarbazepine acetate 900 mg once-daily (o.d.) or eslicarbazepine acetate 450 mg twice-daily (b.i.d.). Tablets with a strength of 450 mg of eslicarbazepine acetate, manufactured by BIAL (S. Mamede do Coronado, Portugal) in accordance with Good Manufacturing Practice, were used.

Blood samples for drug plasma assays were taken at the following times:

Phase A:
pre-dose, and ½, 1, 1½, 2, 3, 4, 6, 8, 12, 24, 36, 48, 72, and 96 hours post-dose;

Phase B:
day 5 to day 11 (inclusive): before the daily dose (for "trough" concentrations assay);
day 12: pre-dose, and ½, 1, 1½, 2, 3, 4, 6, 8, 12, 24, 36, 48, 72, 96, and 120 hours post-dose.

Blood samples were drawn either by direct venipuncture or via an intravenous catheter into lithium heparin tubes and centrifuged at approximately 1500 g for 10 minutes at 4° C. The resulting plasma was separated into 2 equal aliquots of 1 mL and stored at −20° C. until required for analysis.

Plasma concentrations of eslicarbazepine acetate, eslicarbazepine, and R-licarbazepine were determined using isocratic liquid chromatography (LC) with single quadrupole mass spectrometric detection (MS).

The method involved the addition of 500 μL of approximately 0.5 μg/mL of 10,11-dihydrocarbamazepine (internal standard prepared in acetonitrile:water, 3:97, v:v) to 250 μL of plasma (centrifuged at 1800 rpm, prior to analysis) in a polypropylene tube. After vortex mixing for 10 seconds, the mixture was transferred to a Schleicher and Schuell C18/100 mg 96 well solid phase extraction plate. Each well was preconditioned with 800 μL methanol, followed by 800 μL acetonitrile and 800 μL acetonitrile:water (3:97, v:v) prior to application of the total sample volume. Each polypropylene tube was then washed with 500 μL acetonitrile:water (3:97, v:v) and the washings transferred to the respective well. The compounds were eluted into a collection plate with 750 μL acetonitrile and the extract evaporated to dryness under oxygen-free nitrogen, at 40° C. All solid phase extraction manipulations were undertaken using the Tomtec QUADRA 96® Model 320 system and a vacuum was applied at each elution step. The final extract was reconstituted in 100 μL of water:methanol (90:10, v:v) and mixed. The collection plate was then centrifuged at approximately 3000 rpm (at approximately 4° C., for approximately 10 minutes) prior to analysis. An aliquot of the final extract (10 μL) was injected onto the LC-MS system.

The LC-MS system used in the analysis consisted of a Perkin Elmer series 200 micro pump, a Perkin Elmer series 200 autosampler, and a Perkin Elmer/Sciex API 150EX single quadrupole mass spectrometer fitted with a Turbo IonSpray® source. Separation was achieved using a LichroCART 250-4 ChiraDex column (β-cyclodextrin, 5 μm), a LichroCART 4-4 ChiraDex column guard column (β-cyclodextrin, 5 μm), a Jones Chromatography 7971 column heater at 50° C., a mobile phase A (0.2 mM sodium acetate, aq) and a mobile phase B (0.2 mM sodium acetate, MeOH). The MS detector was operated in positive ion mode with mass transitions for BIA 2-093, eslicarbazepine, R-licarbazepine, and the internal standard of 319.16 amu (200 ms), 277.08 amu (200 ms), 277.08 amu (200 ms) and 261.05 amu (200 ms), respectively. The limit of quantification of the assay was 10 ng/mL for eslicarbazepine acetate and 100 ng/mL for eslicarbazepine and R-licarbazepine.

Eslicarbazepine acetate, (S)-(−)-10-acetoxy-10,11-dihydro-5H-dibenz/b,f/azepine-5-carboxamide; eslicarbazepine, (S)-(+)-10,11-dihydro-10-hydroxy-5H dibenz/b,f/azepine-5-carboxamide; and R-licarbazepine, (R)-(−)-10,11-dihydro-10-hydroxy-5H dibenz/b,f/azepine-5-carboxamide, were synthesized in the Laboratory of Chemistry, BIAL, with purities >99.5%. The internal standard, 10,11-dihydrocarbamazepine was supplied by Sigma-Aldrich (St. Louis, Mo.).

The pharmacokinetic parameters were derived from non-compartmental analysis using WinNonlin (Version 4.0, Pharsight Corporation, Mountain View, Calif.). The following parameters were derived, where appropriate, from the individual plasma concentration-time profiles: maximum observed plasma concentration ($C_{max}$); time of occurrence of $C_{max}$ ($t_{max}$); area under the plasma concentration versus time curve (AUC) from time zero to the last sampling time (t) at which concentrations were at or above the limit of quantification ($AUC_{0-t}$), calculated by the linear trapezoidal rule; AUC over the dosing interval ($AUC_\tau$), i.e., 24 hours and 12 hours in the once-daily and the twice-daily group, respectively; AUC from time zero to infinity ($AUC_{0-\infty}$), calculated from $AUC_{0-t}+(C_{last}/\lambda_Z)$, where $C_{last}$ is the last quantifiable concentration; apparent terminal rate constant ($\lambda_Z$) calculated by log-linear regression of the terminal segment of the plasma concentration versus time curve; apparent terminal half-life ($t_{1/2}$), calculated from $\ln 2/\lambda_Z$.

Actual sampling times were used for the pharmacokinetic analysis. Where an AUC was extrapolated to infinity, the percentage of the extrapolated area to the total area was assessed; if greater than 20%, the AUC value was flagged as unreliable. Plasma concentrations below the limit of quantification of the assay (BLQ) were taken as zero for all calculations. All calculations were made using raw data. Values for $t_{max}$ were displayed as nominal times.

Summary statistics for each group and schedule sampling time were reported, as appropriate, using the geometric mean, arithmetic mean, standard deviation (SD), coefficient of variation (CV), median, minimum, and maximum. Comparisons between elderly versus young groups for the single-dose and multiple-dose data were based on analysis of variance (one-way ANOVA) of the logarithmic transformed $C_{max}$, $AUC_\tau$ and $AUC_{0-\infty}$ parameters. A $t_{max}$ comparison between age groups was performed assuming a non-parametric approach using the Wilcoxon signed rank test. In addition, differences in logarithmic transformed parameters ($C_{max}$, $AUG_\tau$ and $AUC_{0-\infty}$) and their associated 95% confidence intervals (95% CI) were estimated between age groups to take the form of ratios on a linear scale. The median values and differences of $t_{max}$ between age groups and 95% CI were reported. All tests of significance were performed at the $p=0.05$ level. The statistical package SAS (Version 8.2, SAS Institute Inc, Cary, N.C.) was used.

Trial B

This human pharmacology trial was a study to determine the pharmacokinetics of eslicarbazepine acetate following single and repeated doses. The study integrated the results of three double-blind, randomized, placebo-controlled trials. To measure the pharmacokinetics of eslicarbazepine acetate following single doses, oral single doses of eslicarbazepine acetate ranging from 20 mg to 2400 mg were administered to healthy young male subjects (6 subjects per dose). The pharmacokinetics of eslicarbazepine acetate following repeated doses were measured by administering repeated oral doses ranging from 400 mg to 2400 mg of eslicarbazepine acetate to healthy young male subjects (6 subjects per dose) over a period of 8 days. Analytical test methods and experimental procedures were similar to those described for Trial A above.

Study Results

Study in Epileptic Patients

Baseline Characteristics

At baseline, the treatment groups were homogenous with regard to age, height, weight, and body mass index. All 143 patients were Caucasian. With respect to gender, there were relatively more female patients in the twice-daily group than in the once-daily and placebo groups (65.2%, 56.0% and 57.4%, respectively); this difference did not significantly affect the results. No significant differences were found in the number of AEDs used: respectively 30.0%, 34.8% and 29.8% of patients in the once-daily, twice-daily, and placebo groups were treated with 1 AED; the remaining patients were treated with 2 AEDs. The most frequently used concomitant AEDs were valproic acid (68.0%, 60.9% and 66.0% of patients in the once-daily, twice-daily, and placebo groups, respectively), topiramate (36.0%, 34.8%, and 21.3%, respectively) and lamotrigine (30.0%, 28.3%, and 31.9%, respectively).

At baseline, mean duration of epilepsy was 16.7, 19.5, and 20.0 years in the once-daily, twice-daily, and placebo groups, respectively. With respect to seizure type frequency, IA simple partial, IB complex partial, and IC partial evolving to secondarily generalized were present in, respectively, 34.0%, 72.0%, and 80.0%, in the once-daily group; 37.0%, 71.7%, and 80.4%, in the twice-daily group; and 27.7%, 80.9%, and 72.3%, in the placebo group. The mean of total number of seizures per month prior to the study was 14.1, 13.6, and 11.8, in the once-daily, twice-daily, and placebo groups, respectively.

Efficacy Results

The proportion of patients with a 50% or greater reduction in seizure frequency in the treatment period compared to the baseline period in the intention-to-treat (ITT) population (n=143) was the primary efficacy endpoint. At the dose of 1200 mg/day (weeks 9-12), the proportion of responders in the once-daily group (54%) was significantly higher (p=0.008) than in the placebo group (28%). The proportion of responders in the once-daily group (54%) was also higher than in the twice-daily (41%) group. At the dose of 800 mg/day (weeks 5-8), the proportion of responders in the once-daily group (58%) was significantly higher (p<0.05) than in the twice-daily (33%) and placebo (38%) groups. At this dose level, no significant difference was found between the twice-daily and the placebo groups.

Secondary endpoints include the reduction in total seizure frequency, proportion of seizure-free patients, distribution of responders, comparison of once and twice daily regimens, and investigator's and patient's global evaluation.

Figure 1:
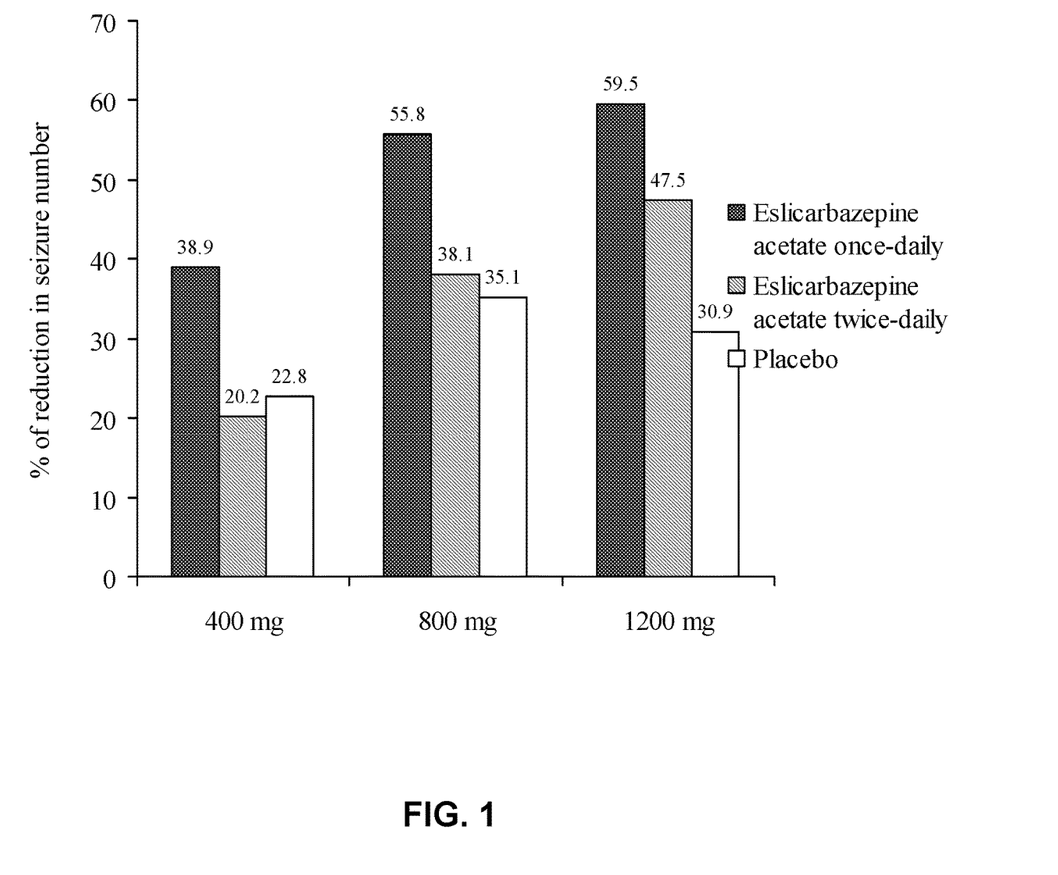
FIG. 1: Percentage reduction in seizure number in each dose period versus baseline (400 mg once-daily versus twice-daily and placebo; 800 mg once-daily versus twice-daily and placebo; 1200 mg once-daily versus twice-daily and placebo).

The greatest decrease in the number of seizures was achieved with 1200 mg and 800 mg once-daily doses, and the results with the once-daily group were better than those obtained in the twice-daily group (FIG. 1). For all dosages (400 mg, 800 mg, and 1200 mg), patients receiving once-daily doses of eslicarbazepine acetate had a substantially greater reduction in the number of seizures compared to patients in the twice-daily and placebo groups.

The number of seizures in patients receiving 1200 mg and 800 mg once-daily doses of eslicarbazepine acetate was reduced by 59.5% and 55.8%, respectively. In comparison, seizures in patients receiving 1200 mg and 800 mg twice-daily doses reduced by 47.5% and 38.1%, respectively. Patients receiving a 400 mg once-daily dose of eslicarbazepine acetate experienced a 38.9% reduction in the number of seizures, almost twice the reduction in seizures observed in patients receiving 400 mg twice-daily doses of eslicarbazepine acetate (20.2%).

At the end of the 12-week treatment phase, 27.9% of the patients in the once-daily dosing group became seizure-free.

In addition, the assessment of efficacy by the investigator (CGI—Clinical Global Impression) and of acceptability by patient was rated best in the once-daily group.

Pharmacokinetic Results

Figure 2:
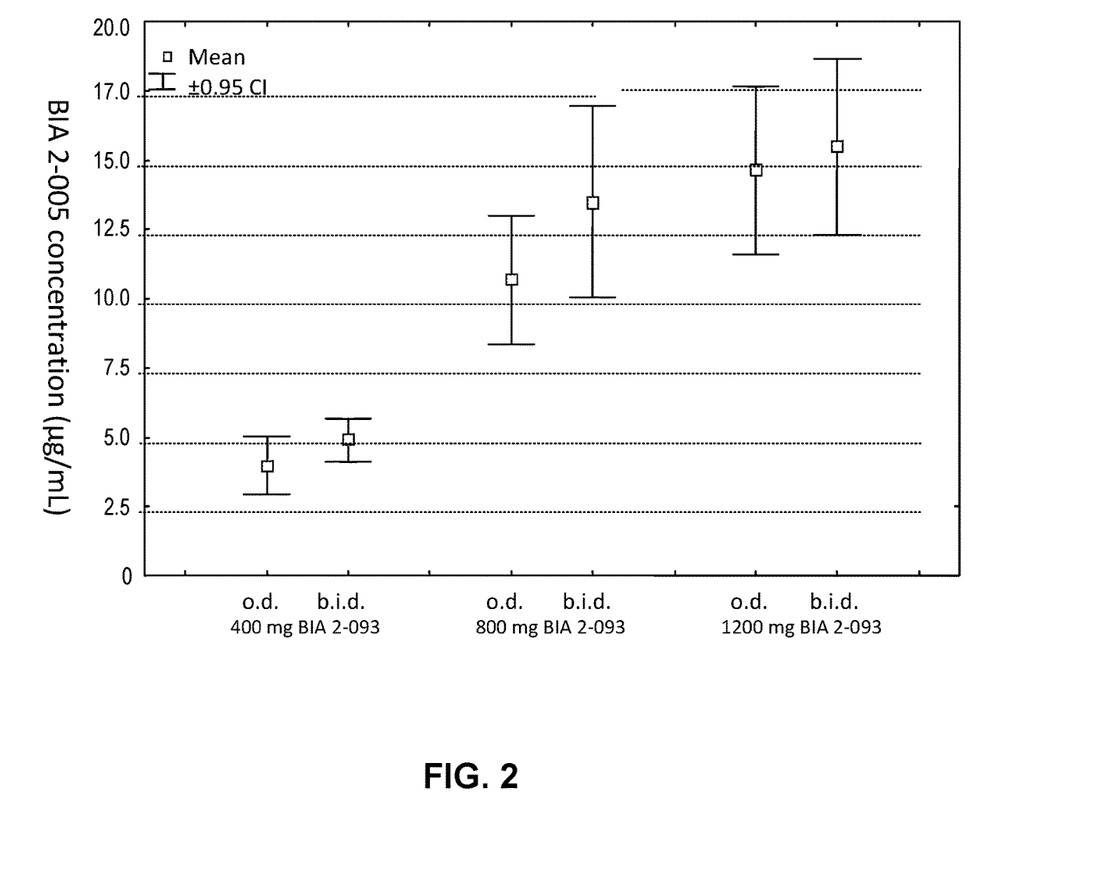
FIG. 2: Mean (95% CI) trough plasma concentrations (μg/mL) of BIA 2-005 following a daily dose of 400 mg, 800 mg and 1200 mg of BIA-2-093 administered once-daily (o.d.) or twice-daily (b.i.d.).

Plasma/serum samples for the "trough" (pre-dose) levels of BIA 2-005 and concomitant AEDs were collected at all visits but V5 (post-study visit). The objective was to characterize the influence of eslicarbazepine acetate on the pharmacokinetic behavior of the concomitant AEDs (e.g., phenytoin, valproate, primidone, phenobarbital, lamotrigine, gabapentin, topiramate, and clonazepam). The mean trough plasma concentrations of BIA 2-005 are displayed in Table 1. As shown in FIG. 2, no significant differences in the BIA 2-005 trough (pre-dose) values between the once-daily and twice-daily groups were found.

TABLE 1

Trough plasma concentrations of BIA 2-005 following oral administration of eslicarbazepine acetate once-daily (o.d.) and twice-daily (b.i.d)

| | 400 mg/day | | 800 mg/day | | 1200 mg/day | |
|---|---|---|---|---|---|---|
| | o.d. group | b.i.d. group | o.d. group | b.i.d. group | o.d. group | b.i.d. group |
| Mean (μg/mL) | 4.0 (3.2) | 4.9 (2.3) | 10.7 (7.0) | 13.5 (9.6) | 14.6 (8.8) | 15.5 (8.8) |

Results expressed as arithmetic means with the correspondent standard deviations (sd) in parenthesis.

The relatively small number of patients being administered phenytoin, primidone, phenobarbital, gabapentin, and clonazepam precluded the appropriate characterization of the eventual effect of eslicarbazepine acetate on the pharmacokinetic behavior of these concomitant AEDs. For valproate, lamotrigine and topiramate, the number of patients was also small, but an exploratory analysis of the effect of eslicarbazepine acetate on the trough blood values of these concomitant AEDs was performed. The mean trough serum concentrations of valproate were not significantly changed by concomitant administration of eslicarbazepine acetate once-daily (7.0%; 95% IC: −7.6, 36.2) or twice-daily (6.3%; 95% IC: −7.5, 20.1). In the placebo group, a significant increase in the serum levels of valproate was noticed (25.4%; 95% IC: 5.1, 45.8). With respect to lamotrigine, its serum levels were not significantly changed when eslicarbazepine acetate once-daily (−10.0%; 95% IC: −46.2, 26.2) or placebo (12.6%; 95% IC: −12.6, 37.8) were added to therapy. With eslicarbazepine acetate twice-daily, the serum levels of lamotrigine decreased significantly (−46.7%; 95% IC: −69.7; −23.8). With respect to topiramate, its serum levels were not significantly changed when eslicarbazepine acetate once-daily (−15.2%; 95% IC: −34.8, 4.4) was added to the therapy. With eslicarbazepine acetate twice-daily, the serum levels of topiramate decreased significantly (−32.4%; 95% IC: −49.5; −15.3). One skilled in the art will know whether a change in serum levels is significant.

Study in Healthy Human Volunteers

Trial A

Pharmacokinetic Results

Eslicarbazepine acetate was shown to be extensively metabolized to eslicarbazepine and, in a minor extent, to R-licarbazepine. The steady-state of eslicarbazepine plasma concentrations was attained at 4 to 5 days of administration in both groups.

Following the last dose, in the once-daily group, mean $C_{max}$ of eslicarbazepine and R-licarbazepine was, respectively, 22,210 ng/mL and 674 ng/mL and occurred at (median $t_{max}$) 2.45 hours and 9.42 hours post-dose, respectively. Mean $AUC_{0-t}$ of eslicarbazepine and R-licarbazepine was 381,601 ng·h/mL and 19,600 ng·h/mL, respectively. In the twice-daily group, mean $C_{max}$ of eslicarbazepine and R-licarbazepine was 16,667 ng/mL and 718 ng/mL, respectively, and occurred (median $t_{max}$) at 2.09 hours and 6.40 hours post-dose, respectively. Mean $AUC_{0-t}$ of eslicarbazepine and R-licarbazepine was 283,014 ng·h/mL and 19,661 ng·h/mL, respectively. Following multiple administration of eslicarbazepine acetate for 8 days, eslicarbazepine was shown to be the major metabolite, representing approximately 95% and 96% of total systemic drug exposure (as assessed by $AUC_{0-24}$) in once-daily and twice-daily subjects, respectively. Tables 2 and 3 depict the eslicarbazepine and R-licarbazepine pharmacokinetic parameters in the once-daily and twice-daily groups following the last dose of eslicarbazepine acetate. The total exposure of healthy volunteers to eslicarbazepine in the once-daily group was unexpectedly at least 26% higher than in the twice-daily group.

TABLE 2

Mean pharmacokinetic parameters of eslicarbazepine and R-licarbazepine following a multiple oral dose of 900 mg eslicarbazepine acetate once-daily.

| | $C_{max}$ (ng/mL) | $t_{max}$ (h) | $AUC_{0-t}$ (ng · h/mL) | $AUC_{0-\tau}$ (ng · h/mL) | $AUC_{0-\infty}$ (ng · h/mL) | $t_{1/2}$ (h) |
|---|---|---|---|---|---|---|
| | Eslicarbazepine | | | | | |
| n | 11 | 11 | 11 | 11 | 11 | 11 |
| $A_{mean}$ | 22210 | 2.45 | 381601 | 294019 | 389344 | 9.12 |
| SD | 7257 | 0.879 | 95368 | 58364 | 97383 | 1.19 |
| | R-licarbazepine | | | | | |
| n | 12 | 12 | 12 | 12 | 12 | 12 |
| $A_{mean}$ | 674 | 9.42 | 19600 | 13397 | 23989 | 15.0 |
| SD | 184 | 6.48 | 6763 | 3187 | 7144 | 3.41 | n = Number of subjects;

$A_{mean}$ = Arithmetic mean;

SD = Standard deviation.

TABLE 3

Mean pharmacokinetic parameters of eslicarbazepine and R-licarbazepine following a multiple oral dose of 900 mg eslicarbazepine acetate twice-daily.

|  | $C_{max}$ (ng/mL) | $t_{max}$ (h) | $AUC_{0-t}$ (ng · h/mL) | $AUC_{0-\tau}$ (ng · h/mL) | $AUC_{0-\infty}$ (ng · h/mL) | $t_{1/2}$ (h) |
|---|---|---|---|---|---|---|
| Eslicarbazepine | | | | | | |
| n | 11 | 11 | 11 | 11 | 11 | 11 |
| $A_{mean}$ | 16667 | 2.09 | 283014 | 142080 | 289792 | 9.17 |
| SD | 3981 | 0.664 | 74203 | 25933 | 74346 | 1.49 |
| R-licarbazepine | | | | | | |
| n | 10 | 10 | 10 | 10 | 10 | 10 |
| $A_{mean}$ | 718 | 6.40 | 19661 | 7783 | 23807 | 14.8 |
| SD | 184 | 3.06 | 6049 | 2083 | 7150 | 4.09 | n = Number of subjects;
$A_{mean}$ = Arithmetic mean;
SD = Standard deviation.

Trial B
Pharmacokinetic Results

As in Trial A, eslicarbazepine acetate was extensively metabolized to eslicarbazepine and, in a minor extent, to R-licarbazepine. The steady-state of eslicarbazepine plasma concentrations was attained at 4 to 5 days of once-daily dosing.

Following the last dose, in the repeated once daily group, mean $C_{max}$ of eslicarbazepine ranged from 8,800 ng/ML· (16.0% coefficient of variation, CV) for 400 mg doses of eslicarbazepine acetate to 56,500 ng·h/ML·(20.0% CV) for 2400 mg doses of eslicarbazepine acetate. The maximum plasma concentration for all dosages occurred (median $t_{max}$) at 2 hours to 3.5 hours. The mean area under the concentration for the dosing interval of 24 hours, $AUC_{0-24h}$, ranged from 126,300 ng·h/ML for 400 mg once-daily doses of eslicarbazepine acetate to 905,900 ng/ML for 2400 mg once-daily doses of eslicarbazepine acetate. Tables 4 and 5 depict the eslicarbazepine and R-licarbazepine pharmacokinetic parameters following the single dose of eslicarbazepine acetate and the pharmacokinetic parameters following the last of the repeated doses of eslicarbazepine acetate.

TABLE 4

Mean pharmacokinetic parameters of eslicarbazepine and R-licarbazepine following single doses of eslicarbazepine acetate (n = 6 subjects per dose group).

| Dose | Mean $C_{max}$ ng/mL (% CV) | Median $t_{max}$ h (range) | Mean $AUC_{0-24\,h}$ ng · h/mL (% CV) | Mean apparent $t_{1/2}$ h (% CV) |
|---|---|---|---|---|
| 20 mg | 300 (18.7) | 0.8 (0.5-0.8) | 2,400 (16.2) | 9.1 (15.9) |
| 50 mg | 900 (24.7) | 0.8 (0.5-2) | 6,700 (12.7) | 8.1 (9.1) |
| 100 mg | 1,500 (13.8) | 1.5 (0.5-2) | 16,400 (11.7) | 9.3 (8.7) |
| 200 mg | 2,900 (16.2) | 1.5 (0.8-2.5) | 30,500 (23.7) | 8.4 (18.8) |
| 400 mg | 5,200 (11.6) | 4 (4-5) | 81,500 (10.8) | 11.7 (18.6) |
| 600 mg | 8,500 (20.0) | 4 (0.5-5) | 119,700 (17.4) | 12.3 (14.8) |
| 900 mg | 15,000 (18.2) | 2.3 (0.8-4) | 210,300 (10.6) | 16.3 (31.9) |
| 1200 mg | 18,600 (16.3) | 4 (2-6) | 285,700 (16.7) | 16.5 (6.8) |
| 1800 mg | 34,600 (16.3) | 3.5 (3-6) | 507,600 (17.0) | 11.8 (11.7) |
| 2400 mg | 35,900 (42.6) | 3 (1.5-6) | 445,600 (26.1) | 11.1 (21.1) |

CV = Coefficient of variation (%);
$C_{max}$ = Maximum plasma concentration;
$AUC_{0-24\,h}$ = Area under the curve of plasma concentration-time over 24 h;
$t_{max}$ = Time to $C_{max}$;
$t_{1/2}$ = Elimination half-life

TABLE 5

Mean pharmacokinetic parameters of eslicarbazepine and R-licarbazepine following the last dose of an 8-day repeated dose regimen of eslicarbazepine acetate (n = 6 subjects per dose group).

| Dose | Mean $C_{max}$ ng/mL (% CV) | Median $t_{max}$ h (range) | Mean $AUC_{0-24\,h}$ ng · h/mL (% CV) | Mean apparent $t_{1/2}$ h (% CV) |
|---|---|---|---|---|
| 400 mg o.d. | 8,800 (16.0) | 3 (0.5-7) | 126,300 (11.7) | 9.50 (18.8) |
| 800 mg o.d. | 18,700 (14.0) | 3.5 (1-7) | 268,400 (10.3) | 12.3 (22.9) |
| 1200 mg o.d. | 25,500 (10.8) | 3 (0.5-6) | 423,000 (10.9) | 13.1 (20.1) |
| 1800 mg o.d. | 47,700 (23.3) | 2 (0.5-4) | 740,300 (19.6) | 11.3 (28.8) |
| 2400 mg o.d. | 56,500 (20.0) | 2 (1.5-8) | 905,900 (12.8) | 10.4 (24.1) |

CV = Coefficient of variation (%);
$C_{max}$ = Maximum plasma concentration;
$AUC_{0-24\,h}$ = Area under the curve of plasma concentration-time over 24 h;
$t_{max}$ = Time to $C_{max}$;
$t_{1/2}$ = Elimination half-life Study Discussion Once-daily administration of eslicarbazepine acetate was found to be more efficacious than the same total dosage divided into twice-daily doses, and is clearly more efficacious in reducing epileptic seizures than placebo. 800 mg and 1200 mg once-daily doses of eslicarbazepine acetate were shown to be noticeably more efficacious in reducing epileptic seizures than twice-daily doses achieving the same total daily dosage.

Eslicarbazepine acetate was shown to be extensively metabolized to eslicarbazepine and, in a minor extent, to R-licarbazepine. Eslicarbazepine represented between 95% and 98% of total systemic drug exposure (as assessed by $AUC_{0-\tau}$, i.e., AUC over the dosing interval) and, therefore, is believed to be mainly responsible for pharmacological activity following administration of eslicarbazepine acetate. Plasma concentrations of parent drug (eslicarbazepine acetate) were systematically found to be below the limit of quantification. With multiple-dosing, steady-state plasma concentrations were attained at 4 to 5 days of administration in both groups, consistent with an effective half-life on the order of about 20-24 hours.

The kinetic profile of eslicarbazepine in the once-daily group was markedly different from the twice-daily group with statistical differences found for some of the pharmacokinetic parameters assessed ($C_{max}$, $AUC_{0-t}$ and $AUC_{0-\infty}$) following multiple oral dosing of eslicarbazepine acetate. In fact, the total exposure of healthy volunteers to eslicarbazepine in the once-daily group was unexpectedly at least 26% higher than in the twice-daily group. This unexpected result is in line with finding in epileptic patients that once-daily administration of eslicarbazepine acetate was more efficacious than the same total daily dosage divided into twice-daily doses. Though this result might imply that the enhanced clinical efficacy would result from an increase in the rate ($C_{max}$) and extent (AUC) of exposure to eslicarbazepine, the reasons for such an enhanced extent of exposure after once-daily versus twice-daily administration remain unexplained.

In addition to the exemplary aspects and embodiments described above, further aspects and embodiments will become apparent to those skilled in the art by study of the foregoing description. Those skilled in the art will recognize that certain modifications of the above description are possible, and such modifications are considered to be within the scope of the invention. It is therefore intended that the following appended claims (including any amendments thereto) and any claims hereafter introduced should be interpreted to include all such aspects, embodiments, and modifications.

The invention claimed is:

1. A method for treating a patient with partial-onset seizures, comprising administering once-daily from about 800 mg to about 1800 mg of eslicarbazepine acetate to the patient, wherein the patient is a human.

2. The method of claim 1, comprising administering once-daily at least about 1200 mg of eslicarbazepine acetate to the patient.

3. The method of claim 1, comprising administering once-daily at least about 1600 mg of eslicarbazepine acetate to the patient.

4. The method of claim 1, comprising administering once-daily from about 800 mg to about 1600 mg of eslicarbazepine acetate to the patient.

5. The method of claim 1, comprising administering once-daily about 800 mg of eslicarbazepine acetate to the patient.

6. The method of claim 1, comprising administering once-daily about 1200 mg of eslicarbazepine acetate to the patient.

7. The method of claim 1, comprising administering once-daily about 1600 mg of eslicarbazepine acetate to the patient.

8. The method of claim 1, wherein the eslicarbazepine acetate is in the form of one or more tablets or oral suspensions.

9. The method of claim 1, wherein the eslicarbazepine acetate is administered orally.

10. The method of claim 1, wherein steady-state plasma concentrations of eslicarbazepine are attained after 4 to 5 days of once-daily administration of the eslicarbazepine acetate.

11. The method of claim 1, wherein upon once-daily administration of the eslicarbazepine acetate, the number, duration, or frequency of seizures in the patient decreases relative to the number, duration, or frequency of seizures in a patient without treatment.

12. The method of claim 1, wherein the once-daily administration of the eslicarbazepine acetate results in a mean maximum plasma concentration, $C_{max}$, of eslicarbazepine from about 18,700 ng/mL to about 47,700 ng/mL.

13. The method of claim 1, wherein the once-daily administration of the eslicarbazepine acetate results in an area under the concentration curve, $AUC_{0-\tau}$, of eslicarbazepine from about 268,400 ng·h/mL to about 740,300 ng·h/mL, wherein $\tau$ is the dosing interval, which is 24 hours.

14. A method for treating a patient with refractory partial-onset seizures, comprising administering once-daily from about 800 mg to about 1800 mg of eslicarbazepine acetate to the patient, wherein the patient is a human experiencing at least four partial-onset seizures per month in spite of treatment with at least one other antiepileptic drug.

15. The method of claim 14, wherein the eslicarbazepine acetate is administered once-daily as adjunctive therapy to a patient being treated with at least one other anti-epileptic drug.

16. The method of claim 15, wherein the at least one other anti-epileptic drug is chosen from phenytoin, valproate, primidone, phenobarbital, lamotrigine, gabapentin, topiramate, clonazepam, and combinations thereof.

17. The method of claim 15, wherein the serum concentration of the at least one other anti-epileptic drug is not significantly decreased by the once-daily administration of the eslicarbazepine acetate.

18. The method of claim 14, comprising administering once-daily at least about 1200 mg of eslicarbazepine acetate to the patient.

19. The method of claim 14, comprising administering once-daily at least about 1600 mg of eslicarbazepine acetate to the patient.

20. The method of claim 14, comprising administering once-daily from about 800 mg to about 1600 mg of eslicarbazepine acetate to the patient.

21. The method of claim 14, comprising administering once-daily about 800 mg of eslicarbazepine acetate to the patient.

22. The method of claim 14, comprising administering once-daily about 1200 mg of eslicarbazepine acetate to the patient.

23. The method of claim 14, comprising administering once-daily about 1600 mg of eslicarbazepine acetate to the patient.

24. The method of claim 14, wherein the eslicarbazepine acetate is in the form of one or more tablets or oral suspensions.

25. The method of claim 14, wherein the eslicarbazepine acetate is administered orally.

26. The method of claim 1, wherein eslicarbazepine acetate is administered once-daily in an initial dose of about 400 mg and increased to a dose of about 800 mg, about 1200 mg, or about 1600 mg.

27. The method of claim 14, wherein eslicarbazepine acetate is administered once-daily in an initial dose of about 400 mg and increased to a dose of about 800 mg, about 1200 mg, or about 1600 mg.

\* \* \* \* \*